(12) United States Patent
Adekenov

(10) Patent No.: US 6,770,673 B1
(45) Date of Patent: Aug. 3, 2004

(54) THERAPEUTIC USES OF ARGLABIN IN COMBINATION WITH OTHER CHEMOTHERAPY AGENTS

(75) Inventor: Sergazy M. Adekenov, Karaganda (KZ)

(73) Assignee: Paracure, Inc., Virginia Beach, VA (US)

( * ) Notice: Subject to any disclaimer, the term of this patent is extended or adjusted under 35 U.S.C. 154(b) by 0 days.

(21) Appl. No.: 09/241,110

(22) Filed: Feb. 1, 1999

Related U.S. Application Data

(62) Division of application No. 08/934,228, filed on Sep. 19, 1997.
(60) Provisional application No. 60/051,681, filed on Jul. 3, 1997.

(51) Int. Cl.$^7$ .......................... A01N 43/08; A61K 31/34
(52) U.S. Cl. .......................... 514/468; 514/90; 514/274; 514/34; 424/649
(58) Field of Search .......................... 424/649; 514/468, 514/34, 274, 90

(56) References Cited

U.S. PATENT DOCUMENTS 5,663,196 A    9/1997   Sari et al. .................... 514/468

FOREIGN PATENT DOCUMENTS

| KZ | N-931984.1 | 8/1993 |
| KZ | 1185 | 12/1993 |
| KZ | 1186 | 12/1993 |
| KZ | 1187 | 12/1993 |
| KZ | 1188 | 12/1993 |
| KZ | 1189 | 12/1993 |
| KZ | 1190 | 12/1993 |
| KZ | 1192 | 12/1993 |
| KZ | 1193 | 12/1993 |
| KZ | 909 | 6/1994 |
| SU | 1746674 | 3/1992 |

OTHER PUBLICATIONS

Barbacid, M., Ann. Rev. Biochem., vol. 56:, pp. 779–827 (1987).
Gibbs et al., Proc. Natl. Acad. Sci. USA, vol. 81, pp. 5704–5708 (Sep. 1984).
Jung et al., Molecular and Cellular Biol., vol. 14, No. 6, pp. 3707–3718 (Jun. 1994).
Marom et al., J. Biol. Chem., vol. 270, No. 38, pp. 22263–22270 (1995).
Prendergast et al., Mol. Cell. Biol., vol. 14, No. 6, pp. 4193–4202 (Jun. 1994).
Shears et al., Biochem. J., vol. 219, pp. 375–382 (1984).
Vogt et al., J. Biol. chem., vol. 270 No. 2, pp. 660–664 (1995).
Adekenov et al., Sesquiterpene lactones from Artemisia glabella, Fitoterapia, vol. LXVI, No. 2, pp. 142–146 (1995).
Bottex–Gauthier et al., Biotechnology Therapeautics, 4 (1&2), pp. 77–98 (1993).
Epstein et al., Proc. Natl. Acad. Sci. USA, vol. 88, pp. 9668–9670 (Nov. 1991).
Adekenov et al., Reactions at the double bond and epoxy group of arglabin, Khim. Prir. Soedin., vol. 1, pp. 33–42, 1991.
Windholz, Editor of The Merck Index, 10$^{th}$ Edition, pp. 329, 394, 408, 599, 1427 and 1428 (1983).
Giordano et al., "The Gastric Cytoprotective Effect of Several Sesquiterpene Lactones," Journal of Natural Products, vol. 53, No. 4. pp. 803–809, Jul.–Aug. 1990.
Blanco et al., "A novel activity for a group of sesquiterpene lactones: inhibition of aromatase" FEBS Letters 409 (1997) pp. 396–400.
Guardia et al., "Mucus Synthesis and Sulfhydryl Groups in cytoprotection mediated by Dehydroleucodine, A Sesquiterpene Lactone," Journal of Natural Products, vol. 57, No. 4, pp. 507–508, Apr. 1994.

*Primary Examiner*—Dwayne C. Jones
(74) *Attorney, Agent, or Firm*—W. Jackson Matney, Jr.; Jenkens & Gilchrist

(57) ABSTRACT

Compositions and kits containing a first chemotherapeutic agent that includes arglabin or a derivative thereof and a second chemotherapeutic agent are described. The compositions and kits are effective for treating cancer in a human patient. Methods for suppressing tumor growth in a human and for reducing the immunodepressive effects of chemotherapeutic agents are also described.

10 Claims, 8 Drawing Sheets

GLABELLIN 17

3-KETO-EUDISM-1(2), 4(5), 11(13)-TRIENE-6-12-OLID 18

ANOBIN 19

3-KETO-10α(14)-EPOXY-1,5,7α(H)4, 6β(H)-GUAI-11(13)-ENE-6-12-OLID

EPOXY ESTAFIATON 20

GAIGRANIN 21

THERAPEUTIC USES OF ARGLABIN IN COMBINATION WITH OTHER CHEMOTHERAPY AGENTS

CROSS REFERENCE TO RELATED APPLICATIONS

This is a divisional application of U.S. patent application Ser. No. 08/934,228, filed on Sep. 19, 1997, which claims the benefit of U.S. Provisional Application No. 60/051,681, filed on Jul. 3, 1997, and Kazakhstan Patent Application No. 97 0397,1, filed on Apr. 26, 1997.

BACKGROUND OF THE INVENTION

Cancer is a leading cause of death in the United States and affects people worldwide. Surgery, radiation and chemotherapy are the most widely used therapeutic modalities. Chemotherapy agents create conditions within the cell that limit cell growth and replication. DNA synthesis may be inhibited by preventing purine biosynthesis, pyrimidine biosynthesis, the conversion of ribonucleotides to deoxyribonucleotides, antimetabolites, intercalation, or cross-links. RNA synthesis, for example, may be inhibited by antimetabolites. Protein synthesis may be inhibited, for example, by agents that deaminate asparagine. Additionally, agents that inhibit the function of microtubules can be used as chemotherapy agents.

Chemotherapy agents typically affect both neoplastic and rapidly proliferating cells of normal tissue such as bone marrow, hair follicles and intestinal epithelium. Anorexia, nausea, vomiting, diarrhea, suppression of bone marrow function and hair loss are some of the negative effects commonly associated with chemotherapy. Development of a chemotherapy agent that is an effective antitumor agent with minimal toxicity would be advantageous.

SUMMARY OF THE INVENTION

It has been discovered that arglabin and various derivatives of arglabin can function as effective chemotherapeutic agents, with fewer side-effects than typically follow from use of other chemotherapeutic agents.

In one aspect, the invention features a composition including a first chemotherapeutic agent that includes arglabin or a derivative thereof and a second chemotherapeutic agent. The second chemotherapeutic agent is not arglabin or a derivative thereof. The composition is effective to suppress tumor growth in a human. A particularly useful arglabin derivative is dimethylaminoarglabin or a pharmaceutically acceptable salt thereof. The second chemotherapeutic agent may be, for example, an alkylating agent such as cyclophosphamide, sarcolysin, or methylnitrosourea, an antimetabolite such as methotrexate or fluorouracil, a vinca alkaloid such as vinblastine or vincristine, an antibiotic such as rubidomycin or a platinum coordination complex such as cisplatin. Two or more chemotherapeutic agents may be in the composition with arglabin or a derivative thereof.

The invention also features a kit including a first container containing a first chemotherapeutic agent including arglabin or a derivative thereof, and a second container containing a second chemotherapeutic agent. The second chemotherapeutic agent is not arglabin or a derivative thereof. A particularly useful derivative of arglabin is dimethylaminoarglabin or a pharmaceutically acceptable salt thereof. The second chemotherapeutic agent may be, for example, an alkylating agent such as cyclophosphamide, sarcolysin, or methylnitrosourea, an antimetabolite such as methotrexate or fluorouracil, a vinca alkaloid such as vinblastine or vincristine, an antibiotic such as rubidomycin or a platinum coordination complex such as cisplatin. Two or more chemotherapeutic agents may be included in the kit.

The invention also features a method of suppressing tumor growth in a human including administering to the human an amount of a first chemotherapeutic agent that includes arglabin or a derivative thereof and a second chemotherapeutic agent effective to suppress the tumor growth in the human. The second chemotherapeutic agent is not arglabin or a derivative thereof. A particularly useful derivative of arglabin is dimethylaminoarglabin or a pharmaceutically acceptable salt thereof. The second chemotherapeutic agent may be, for example, an alkylating agent such as cyclophosphamide, sarcolysin, or methylnitrosourea, an antimetabolite such as methotrexate or fluorouracil, a vinca alkaloid such as vinblastine or vincristine, an antibiotic such as rubidomycin or a platinum coordination complex such as cisplatin.

In another aspect, the invention features a method for reducing the immunodepressive effect of a chemotherapy agent in a human. The method includes administering to the human an amount of arglabin or a derivative thereof under conditions effective for augmenting the immune system of the human upon treatment of the human with the chemotherapy agent. A particularly useful derivative of arglabin is dimethylaminoarglabin or a pharmaceutically acceptable salt thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE PREFERRED EMBODIMENTS

Figure 8A:
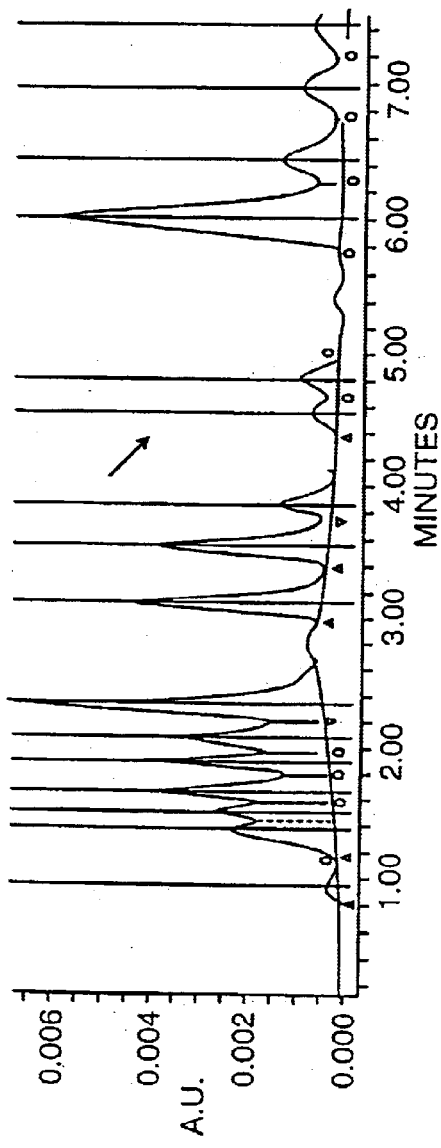
Figure 8B:
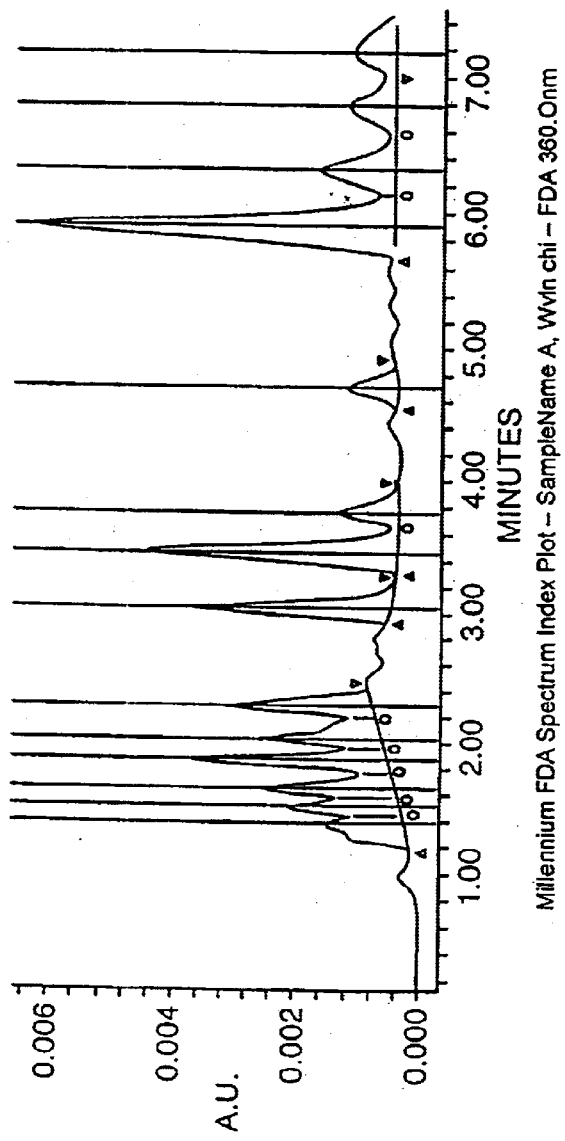

FIG. 8 is a spectrum index plot of naphthol cleavage products. FIG. 8A is in the absence of drug. FIG. 8B is in the presence of drug.

DESCRIPTION OF THE PREFERRED EMBODIMENTS

The invention provides novel compounds that suppress tumor growth in humans. These compounds may be synthesized from the parent compound arglabin (FIG. 1), which is isolated from *Artemisia glabella*. Various arglabin derivatives may be made using a range of chemistries. For example, epoxyarglabin may be produced by epoxidation of the tri-substituted olefin double bond with peracetic acid. Dichlorohydrins may be produced by treatment of epoxyarglabin with an ether-acetone HCl solution. Dibromoarglabin may be produced by reacting arglabin with $Br_2$ and carbontetrachloride. Arglabin chlorohydrins may be produced from arglabin by reaction with a methanol hydrochloride solution. Epoxidation of arglabin chlorohydrins with peracetic acid and chloroform results in chromatographically separable epoxyarglabin chlorohydrins. Arglabin diol, its isomer and diene may be produced by hydrolyzing arglabin. The 1,10 epimer of arglabin, epiarglabin may be produced by treatment of arglabin diol with $POCl_3$. Benzylaminoarglabin and benzylaminoepoxyarglabin may be produced by treatment of arglabin and epoxyarglabin with benzeneamine. Dimethylaminoarglabin and dimethylaminoepoxyarglabin may be produced by treatment of arglabin and epoxyarglabin with dimethylamine. Morpholine-aminoarglabin and morpholine-aminoepoxyarglabin may be produced by amination of arglabin with morpholine. Pharmaceutically acceptable salts of these compounds may be produced with standard methods and used as antitumor agents. For example, dimethylaminoarglabin hydrochloride and dimethylaminoepoxyarglabin hydrochloride may be produced by hydrochlorination. Dihydroarglabin may be produced by treating arglabin with ethanol and $H_2/Ni$. The various arglabin derivatives set out above are depicted in FIGS. 1–4.

The invention also relates to a method of suppressing tumor growth in a human patient diagnosed with cancer comprising administering arglabin or a derivative thereof to the patient. While this method may be used generally for the treatment of cancers such as breast, colon, rectal, stomach, pancreatic, lung, liver, ovarian, pancreatic and esophageal cancer, leukemia and lymphomas, certain types of cancers, such as lung, liver and ovarian cancer, are particularly amenable to this therapeutic regimen. The compounds can be administered topically, orally, intravenously, intraperitoneally, intrapleurally, intrathecally, subcutaneously, intramuscularly, intranasally, through inhalation or by suppository, depending on the type of cancer and on various patient indications. For example, intraperitoneal administration may be used for some patients with ascites. Intrapleural administration may be used for certain patients with-lung cancer. Suppositories may be used for patients with rectal cancer. Arglabin or a derivative thereof may be administered in a daily amount from about 40 mg to about 480 mg, preferably from about 175 mg to about 315 mg, more preferably from about 240 mg to about 280 mg. Typically the dosage ranges from about 0.5 mg/kg to about 7 mg/kg. In extreme conditions, up to about 20 mg/kg of arglabin or a derivative thereof may be administered. Once administered, these compounds act as antitumor agents and may inhibit the growth of the tumor or may cause the tumor to regress.

Without being bound by any particular biochemical mechanism, these compounds may eliminate or inhibit the growth of cancer cells by impeding farnesylation of proteins such as the ras protein. The ras gene is a protooncogene that plays a role in many types of human cancers, including colorectal carcinoma, exocrine pancreatic carcinoma, and myeloid leukemias (Barbacid, 1987, Ann. Rev. Biochem. 56:779). Approximately 20 to 30% of all human tumors can be attributed to the activation of the ras protooncogene. Ras genes constitute a multi-gene family that transform cells through the action of a 21 kDa protein termed ras p21 (also referred to herein as "ras"). Ras functions as a G-regulatory protein, hydrolyzing GTP to GDP. In its inactive state, ras binds GDP. Upon activation of growth factor receptors, ras exchanges GDP for GTP and undergoes a conformational change. In its GTP-bound state, the wild-type ras couples the signals of activated growth factor receptors to downstream mitogenic effectors. The intrinsic GTP-ase activity of ras eventually returns the protein to its inactive GDP-bound state. In tumor cells, a mutation in the ras gene results in a loss of regulatory function, resulting in constitutive transmission of growth stimulatory signals and oncogenic activation.

For both normal and oncogenic functions, ras must be localized at the plasma membrane, a process that is dependent upon proper post-translational processing of the ras (Hancock, 1989, Cell 57:1167). In the first step in the post-translational processing of ras, a farnesyl group is attached to a cysteine residue at position 186 of the protein by reaction with farnesyl pyrophosphate. Second, the carboxy-terminal three amino acids of the protein are cleaved by the action of a specific protease. Third, the carboxylic acid terminus is converted to a methyl ester by alkylation with a methyl group.

Post-translational modification of ras is mediated by an amino acid sequence motif frequently referred to as a "CAAX box." In this sequence motif, C represents Cysteine, A represents an aliphatic amino acid, and X is another amino acid such as Methionine, Serine, or Glutamine. Depending on the specific sequence of the CAAX box, this motif serves as a signal sequence for farnesyl-protein transferase or geranylgeranyl-protein transferase, which catalyze the alkylation of the cysteine residue of the CAAX sequence. Farnesylation of ras is required for proteolytic processing, palmitoylation, and tight binding of the ras protein to cellular membranes.

In the absence of farnesylation, oncogenic forms of ras cannot oncogenically transform cells. Indeed, inhibitors of farnesyl-protein transferase have been shown to block the growth of ras-transformed cells in soft agar. Accordingly, inhibitors of farnesyl-protein transferase, and of ras activity in general, are thought to be useful anti-cancer therapeutics for many types of cancers (Gibbs et al., 1984, Proc. Natl. Acad. Sci. USA 81:5704–5708; Jung et al., 1994, Mol. Cell. Biol. 14:3707–3718; Predergast et al., 1994, Mol. Cell. Biol. 14: 4193–4202; Vogt et al., 1995, J. Biol. Chem. 270: 660–664; and Maron et al., 1995, J. Biol. Chem. 270: 22263–22270).

As described below, arglabin and derivatives thereof appear to inhibit protein farnesylation.

In an alternative embodiment, a pharmaceutical composition containing from about 40 mg to about 480 mg, preferably from about 175 mg to about 315 mg, more preferably from about 240 to about 280 mg of arglabin or a derivative thereof is provided in unit dosage form. The dose may be divided into 2–4 daily doses. Typical dosages of these pharmaceutical composition range from about 0.5 mg/kg to about 7 mg/kg. In extreme conditions, up to about 20 mg/kg may be administered. Lyophilized dimethylaminoarglabin and lyophilized pharmaceutically acceptable salts such as dimethylaminoarglabin hydrochloride are particularly useful as pharmaceutical compositions. The optimal concentration of arglabin or a derivative thereof in a pharmaceutically acceptable composition may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the type and extent of cancer metastases, the overall health status of the particular patient and the relative biological efficacy of the compound selected. These compositions may be used for the treatment of cancer, especially lung, liver and ovarian cancer, although other cancers such as breast, rectal, colon, stomach, pancreatic or esophageal cancer are also beneficially treated with the compositions. In addition, hematopoietic cancers such as leukemias and lymphomas may also be beneficially treated.

Compounds of the invention may be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

A compound of the invention may be conveniently administered in unit dosage form, and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils of vegetable origin, hydrogenated naphtalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as a gel to be applied intranasally. Formulations for parenteral administration may also include glycocholate for buccal administration.

The invention also relates to an article of manufacturing containing packaging material and arglabin or a derivative thereof contained within the packaging material. Arglabin or a derivative thereof are therapeutically effective for suppressing tumor growth in a human. The packaging material contains a label or package insert indicating that arglabin or a derivative thereof may be used for suppressing tumor growth in a human. Dimethylaminoarglabin and pharmaceutically acceptable salts thereof are arglabin derivatives that are particularly useful in the article of manufacturing.

In an alternate embodiment, the invention relates to compositions and kits comprising a first chemotherapeutic agent including arglabin or a derivative thereof and a second chemotherapeutic agent. The second chemotherapeutic agent is not arglabin or a derivative thereof. These compositions are effective to suppress tumor growth in a human. Dimethylaminoarglabin or a pharmaceutically acceptable salt thereof is a particularly useful derivative of arglabin. Various classes of chemotherapeutic agents, including alkylating agents, antimetabolites, vinca alkaloids, antibiotics or platinum coordination complexes may be used in the composition. For example, alkylating agents such as the nitrogen mustards cyclophosphamide and sarcolysin may be used, although other alkylating agents such as methylnitrosourea are also appropriate. Antimetabolites such as the folic acid analog methotrexate or pyrimidine analogs such as fluorouracil or 5-fluorouracil may be used, as well as vinca alkaloids such as vinblastine or vincristine. An antibiotic such as rubidomycin can be an appropriate chemotherapeutic agent, as well as platinum coordination complexes such as cisplatin. Multiple chemotherapeutic agents may be combined with arglabin or a derivative thereof. For example, vincristine and cyclophosphamide or vincristine and vinblastine may be combined with arglabin or a derivative thereof.

The invention also relates to a method of suppressing tumor growth in a human patient by administering to the patient an amount of a composition including a first chemotherapeutic agent including arglabin or a derivative thereof and a second chemotherapeutic agent effective to suppress tumor growth in the human. The second chemotherapeutic agent is not arglabin or a derivative thereof. These compositions provide an enhanced antitumor effect and may also prevent development of metastases. In particular, these compositions are useful for overcoming tumors that are drug-resistant. The agents may be administered separately or as a cocktail. Toxicity may be reduced by administering arglabin or a derivative thereof several hours prior to administering the chemotherapy agent. The compositions may be administered by any route.

The invention also relates to a method for reducing the immundepressive effect of a chemotherapy agent in a human patient by administering to the patient an amount of arglabin or a derivative thereof effective to augment the immune system of the patient upon treatment of the patient with the chemotherapy agent. The immune system may be augmented, for example, by increasing the total number of leukocytes, T-lymphocytes, B-lymphocytes, or immunoglobulins.

The invention will be further described in the following examples, which do not limit the scope of the invention described in the claims.

EXAMPLES

Example 1: Isolation of Arglabin

The smooth wormwood *Artemisia glabella* Kar. et Kir. is a perennial plant that is widespread on the Kazakhstan dry steppe hills. The aerial parts of *A. glabella*, including the leaves, buds, flower buds and stems, contain sesquiterpene lactones including arglabin throughout the vegetation stage of the plant (Table I).

TABLE I

| Vegetation phase | Plant organ | Dry plant (g) | Isolated arglabin (g) | Arglabin in dry plant (%) |
|---|---|---|---|---|
| Rosette | leaves | 1900 | 6.4 | 0.34 |
| Buttonization | leaves | 1000 | 6.1 | 0.61 |
| | stems | 1700 | 1.28 | 0.08 |
| | buds | 1000 | 6.0 | 0.60 |

A variety of solvents were used to extract sesquiterpene lactones from the dry plant material (Table II). It was found that extracting the lactones from the flowering stage of the plant with chloroform three times at 45–50° C. produced the highest yield.

TABLE II

| Solvent | Extracted Material (g) | Isolated Lactones | Lactones % in Dry plant |
|---|---|---|---|
| Water | 1.5 | arglabin | 0.002 |
|  |  | argolide | traces |
|  |  | dihydrogarglolide | traces |
| Petrol-diethyl ether 1:1 | 3.2 | arglabin | 0.002 |
|  |  | argolide | traces |
|  |  | dihydrogarglolide | traces |
| Benzene | 3.4 | arglabin | traces |
| Diethyl ether | 4.8 | arglabin | 0.11 |
|  |  | argolide | 0.007 |
|  |  | dihydrogarglolide | traces |
| Chloroform | 6.7 | arglabin | 0.150 |
|  |  | argolide | 0.0075 |
|  |  | dihydrogarglolide | 0.0006 |
| Ethanol | 5.1 | arglabin | 0.08 |
|  |  | argolide | 0.01 |

An extraction device consisting of a counter-flow continuous extractor, loading device and three vessels isolated from the exterior environment was used for the extractions. The solvent vessel has a filter, distillator with an evaporator and condenser, and a buffer capacity. The drying agent vessel consists of a dryer, cyclone, cooler, ventilator and heater. The cooling water vessel includes a saltpan with ventilation. The extraction device also has a deodorizer with ventilator, a waste tank and an extract collector.

Approximately 7.7 kg of dry material from *Artemisia glabella* Kar. et Kir. was placed in the extraction device and continuously mixed with solvent as the material was moved through the extractor column. The solvent moves in the opposite direction of the dry plant material and gradually becomes saturated with extracted substances. As the saturated solvent was discharged, it was first filtered to remove plant material particles, then evaporated. The filtered plant particles were recirculated through the extractor for re-extraction. Vapors from the evaporation were sent to the condenser. From the condenser, pure solvent was recovered and recirculated to the extraction device. Condensation surfaces in the condenser were cooled with water pumped from the salt pan where the water was previously cooled with exterior air blown in the ventilator. Due to air-vaporized cooling in the salt pan, the water may be cooled down to temperatures considerably lower than the ambient temperature.

The extracted substances refined from the solvent are in the form of a tar. During this process, approximately 7% of the plant material (539 grams) was recovered.

The tar was further refined by addition of two volumes (approximately 1.08 L) of 60° C. ethanol with continuous stirring to dissolve the tar. Distilled water, heated to approximately 70° C., was added in a ratio of about 2:1 alcohol to water. The tar-alcohol-water solution was thoroughly stirred for 30 minutes, then left at room temperature for approximately 24 hours or until a precipitate was formed. The water alcohol solution was filtered through a ceramic filter under vacuum. The procedure was repeated with any precipitate remaining after filtration.

The filtrate was rotary evaporated and the alcohol was vacuum distilled in the form of an azeotropic mixture with water containing 68–70% alcohol. After distillation of the alcohol, the water solution yielded approximately 286 grams of refined tar.

The refined tar was separated into individual components over a KCK silicagel column, with pressure, using benzene as the eluant. Benzene fractions were collected and analyzed for arglabin using thin-layer chromatography (TLC) (silufol, benzene-ethanol, 9:1). Arglabin-containing fractions were distilled to remove benzene. Arglabin at this stage has a yellow color. Approximately 33 g of arglabin was produced, with a yield of about 11.7%.

Arglabin was recrystallized by dissolving in hexane in a 1:10 ratio of product to hexane (w/v) and heating. After arglabin was in solution, the product was vacuum filtered. Crystals of arglabin were isolated from the filtrate at room temperature. Approximately 21 g of arglabin was recovered from this step. Arglabin has a structure of 1(R), 10(S)-epoxy-5(S), 6(S), 7(S)-guaia-3(4), 11(13)-diene-6,12-olide. The stereochemistry of arglabin was determined through x-ray analysis.

The joining of the pentene and heptane ring and heptane and γ-lactone rings into two crystallographically independent molecules of arglabin is transoid. Torsion angles of $O_3C_1C_5H_5$ are −142(1) and −136(2)°, and $H_6C_6C_7H_7$ are −167(2) and −159(3)°, respectively. The pentene ring accepts the conformation of the 1α-envelope ($\Delta C^1_s$=2.9 and 1.5°) and the heptane ring is 7α,1,10β-chain ($\Delta C^7_s$=2.7 and 4.7°). The methyl group by the C-10 atom has an equatorial-α-orientation. Conformation of γ-lactone ring was between 7α-envelope and 6β,7α-semichair but was closer to the latter ($\alpha C^{12}_2$=2.0 and 6.1°).

The NMR spectrum of arglabin was recorded on a Varian HA-100D apparatus in CDCl. Chemical shifts are given in δ-scale from signal TMC accepted for 0. There are two three-proton singlets at 1.34 (methyl at epoxide) and at 1.94 ppm (methyl at double bond). A single-proton doublet was registered at 2.95 ppm with J=10 Hz (proton at C). A single-proton triplet was detected with the center at 3.97 ppm with J=10 Hz (lactone proton). Two single-proton doublets were obtained at 5.42 ppm with J=3 Hz and 6.1 ppm with J=3 Hz (exomethylene at lactone cycle) and a single-proton signal at 5.56 (vinyl protons). The structure of arglabin (FIG. 1) was confirmed on the basis of the NMR spectrum of the isolated compound and that of related sesquiterpene lactones arborescien and ludartine.

Summary of arglabin characteristics: Colorless, Melting Point of approximately 100–102° C. (hexane); $[\alpha]^2_D$+45.6° (c 0.3, CHCl$_3$); IR bands (KBr) 1760, 1660, 1150, 1125 cm$^{-1}$; $^1$H-NMR (400 MHz, CDCl$_3$) δ 1.34 (3H, s, H-14), 1.94 (3H, s, H-15), 2.95 (1H, d, J 10 Hz, H-5), 3.97 (1H, t, J 10 Hz, H-6), 5.56 (1H, br s, H-3), 5.42 (1H, d, J 3 Hz, H-13a), 6.10 (1H, d, J 3 Hz, H-13b).

Example 2: Arglabin Derivatives

To assist the reader, the names of the various compounds set out below are followed with numerals to facilitate identification with the compounds depicted in the Figures.

Reagents affecting the epoxide or olefin group of arglabin were used to derivatize arglabin. Epoxidation of the tri-substituted olefin double bond of arglabin 1 with peracetic acid (FIG. 1) proceeded with high yield and 95% stereoselectivity, forming 3β,4β-epoxyarglabin 2 (1(10), 3(4)-diepoxy-guai-11(13)-en-6,12-olid). Silica gel column chromatography with ethylether was used to recover epoxyarglabin 2 with an approximate 65% yield. IR and NMR spectra were used to confirm the structure of epoxyarglabin 2.

Summary of epoxyarglabin 2 characteristics: Melting point of 149–151° C. (Et$_2$O—CH$_2$Cl$_2$); $[\alpha]^{22}_D$+94.0° (c 1.7, CHCl$_3$); IR bands (KBr) 1760, 1670 cm$^{-1}$; $^1$H-NMR (400 MHz, py-d$_5$) δ 1.30 (3H, s, H-14), 1.68 (3H, s, H-15), 3.31 (1H, s, H-3, 4.11 (1H, t, J 10 Hz, H-6), 5.43 (1H, d, J 3 Hz, H-13a), 6.16 (1H, d, J 3 Hz, H-13b).

Figure 1:
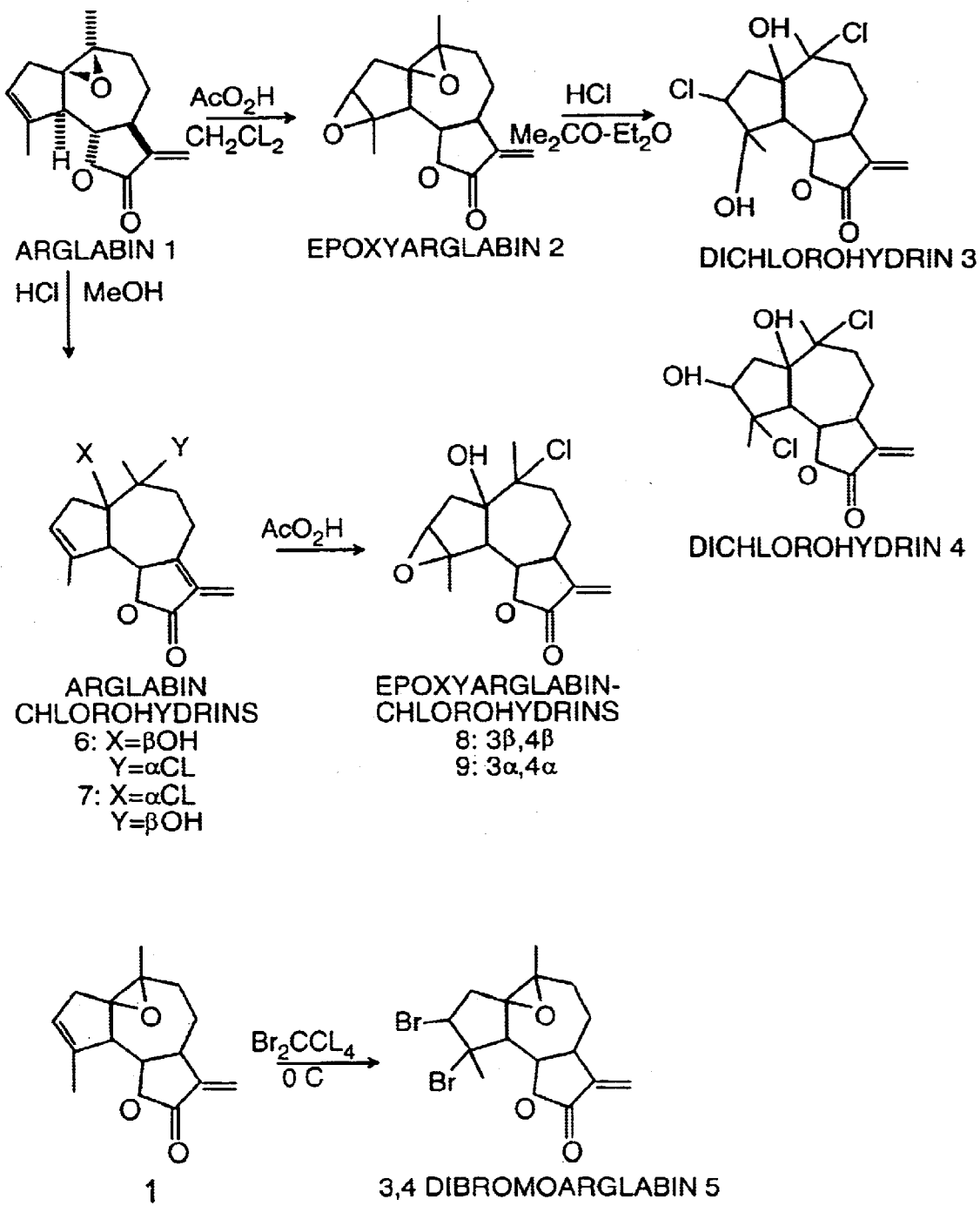
FIG. 1 depicts the synthesis of arglabin derivatives 2 through 9.

Treatment of epoxyarglabin 2 with an ether-acetone HCl solution produced dichlorohydrines 3 and 4 (FIG. 1). An opening of both epoxygroups with a yield of 60% and 95% regioselectivity was observed. Dichlorohydrines 3 and 4 were diluted with water, washed with NaHCO$_3$, and purified by silica gel column chromatography using Et$_2$O-iPr$_2$O in a 1:1 ratio. IR and NMR spectral data were used to confirm the structure.

Summary of dichlorohydrines 3 and 4 characteristics: 3 (60%) melting point 190–191° C.; [α]$^{20}{}_D$–90.1° (c 0.34 acetone); IR bands (KBr) 3465, 1750, 1670 cm$^{-1}$; $^1$H-NMR (400 MHz, py-d$_5$) δ 1.61 (3 Hz, s, H-14), 1.62 (3H, s H-15), 4.42 (1H, dd, J10, 7 Hz, H-3), 4.48 (1H, t, J 10 Hz, H-6), 5.52 (1H, d, J 3 Hz, H-13a), 6.04 (1H, d, J 3 Hz, H-13b). 4 (5%) melting point 176–178° C. (CH$_2$Cl$_2$—Et$_2$O); [α]$^{24}{}_D$+ 23.25° (c 0.43, CHCl$_3$); IR bands (KBr) 3680, 1770, 1670 cm$^{-1}$; $^1$H-NMR (400 MHz, py-d$_5$) δ 1.41 (3H, s, H-14); 1.57 (3H, s, H-15), 3.39 (1H, d, J 10 Hz, H-5), 3.42 (1H, s, 10-OH), 4.05 (1H, d, J 5.5 Hz, H-3), 4.40 (1H, s, 4-OH), 4.55 (1H, t, J 10 Hz, H-6), 5.54 (1H, d, J 3 Hz, H-13a), 6.21 (1H, d, J 3 Hz, H-13b).

Other derivatives were generated by bromination and interaction with N-bromosuccinimide in aqueous acetone, resulting in the formation of mobile bromohydrines on trisubstituted double bonds and partial bromination of the exomethylene group. 3,4 Dibromoarglabin 5 was produced by treating arglabin 1 with Br$_2$ and carbontetrachloride at 0° C.

Treatment of arglabin 1 with a methanol HCl solution gave a chromatographically separable mixture of chlorohydrines 6/7 in an approximate 6:1 ratio with high yield (FIG. 1). Simultaneously, partial attachment of HCl elements to the exomethylene double bond was observed by a Michael type reaction. Epoxidation of the prevailing regioisomer 6 with peracetic acid in chloroform resulted in a mixture of chromatographically separable isomer epoxyarglabin chlorohydrins 8/9 in a 1:1 ratio. Structures of previously unknown chlorohydrines 6–9 were established on the basis of elemental and spectral analyses, taking into consideration the results of epoxide 8 by x-ray.

Figure 2:
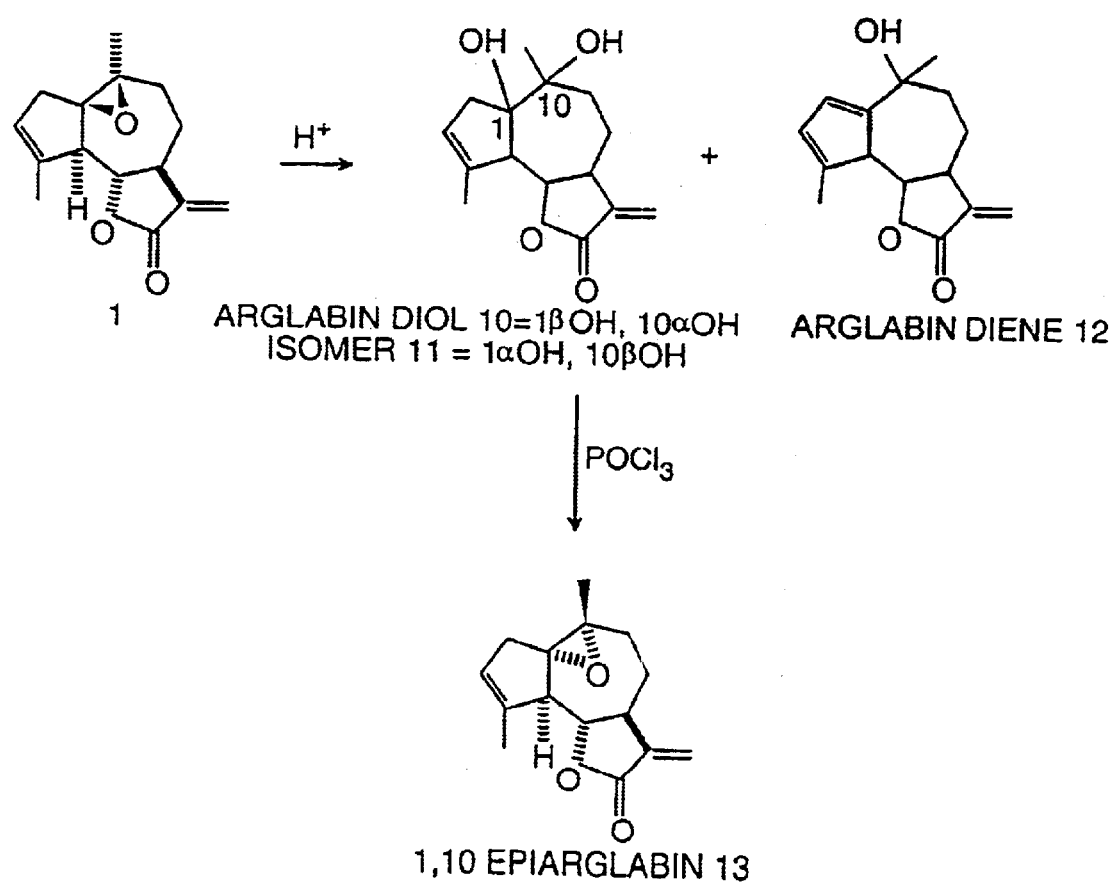
FIG. 2 depicts the synthesis of arglabin derivatives 10 through 13.

Reflux of about 550 mg of arglabin 1 with approximately 15 ml of acetonitrile and a drop of HBF$_4$ for 1.5 hour resulted in diol 10 as the major product, and its isomer 11 and the diene 12 in lower yield (FIG. 2). The reactions were neutralized, diluted with water, extracted with chloroform, then purified by column chromatography (10, petrol-ethyl ether 2:1; 11, petrol-ethyl ether 1:1; 12, petrol-ethyl ether 1:3).

Summary of diol 10, isomer 11 and diene 12 characteristics: 10 melting point 184–185° C. (ethyl ether); [α]$^{21}{}_D$+ 72.3° (c 0.3, CHCl$_3$); IR bands (KBr) 3440, 1770, 1680 cm$^{-1}$; $^1$H-NMR (400 MHz, py-d$_5$) δ 1.30 (3H, s, H-14), 1.92 (3H, br s, H-15), 4.18 (1H, dd, J 10, 1 Hz, H-6), 5.43 (1H, br s, H-3), 5.38 (1H, d, J 3.5 Hz, H-13a), 6.14 (1H, d, J 3.5 Hz, H-13b). 11: mp 149–151° C. (CHCl$_3$—Et$_2$O); [α]$^{25}{}_D$+ 108.6° (c 0.3, CHCl$_3$; IR bands (KBr) 3460, 1770, 1670 cm$^{-1}$; $^1$H-NMR (400 MHz, py-d$_5$) δ 1.35 (3H, s, H-14), 1.92 (3H, br s, H-15), 3.10 (1H, d, J 10 Hz, H-5), 4.39 (1H, t, J 10 Hz, H-6), 5.48 (1H, br s, H-3), 5.44 (1H, d, J 3.5 Hz, H-13a), 6.14 (1H, d, J 3.5 Hz, H-13b). 12: melting point 220–222° C. (EtOH); [α]$^{22}{}_D$+80.6° (c 0.57, CHCl$_3$); IR bands (KBr) 3350, 1770, 1680, 1550 cm$^{-1}$; $^1$H-NMR (400 MHz, py-d$_5$) δ 1.47 (3H, s, H-14), 1.92 (3H, br s, H-15), 4.32 (1H, t, J 10.5 Hz, H-6), 5.24 (1H, br s, H-2), 5.50 (1H, br s, H-3), 5.41 (1H, d, J 3.5 Hz, H-13a), 6.15 (1H, d, J 3.5 Hz, H-13b).

The 1,10-epimer of arglabin, epiarglabin 13 was synthesized by adding approximately 0.1 ml of POCl$_3$ to a cooled solution (approximately 0° C.) of 120 mg of diol 10 in pyridine. (FIG. 2) After stirring for 24 hours at approximately –5° C., the reaction was worked up by extraction with ethyl ether. After washing with 5% HCl and water, the residue was crystallized from petroleum ethyl ether to give 40 mg of 1,10-epiarglabin 13.

Summary of 1,10-epiarglabin 13 characteristics: melting point 193–194° C. (EtOH); [α]$^{20}{}_D$+78.40 (c 0.43, CHCl$_3$); IR bands (KBr) 1760, 1665, 1650, 1150 cm$^{-1}$; $^1$H-NMR (400 MHz, py-d$_5$) δ 1.30 (3H, s, H-14), 1.90 (3H, br s, H-15), 2.66 (1H, m, H-5), 4.18 (1H, dd, J 14.5, 12.5 Hz, H-6), 5.43 (1H, m, H-3), 5.38 (1H, m, H-3), 6.14 (1H, d, J 3.5 Hz, H-13b).

Figure 3:
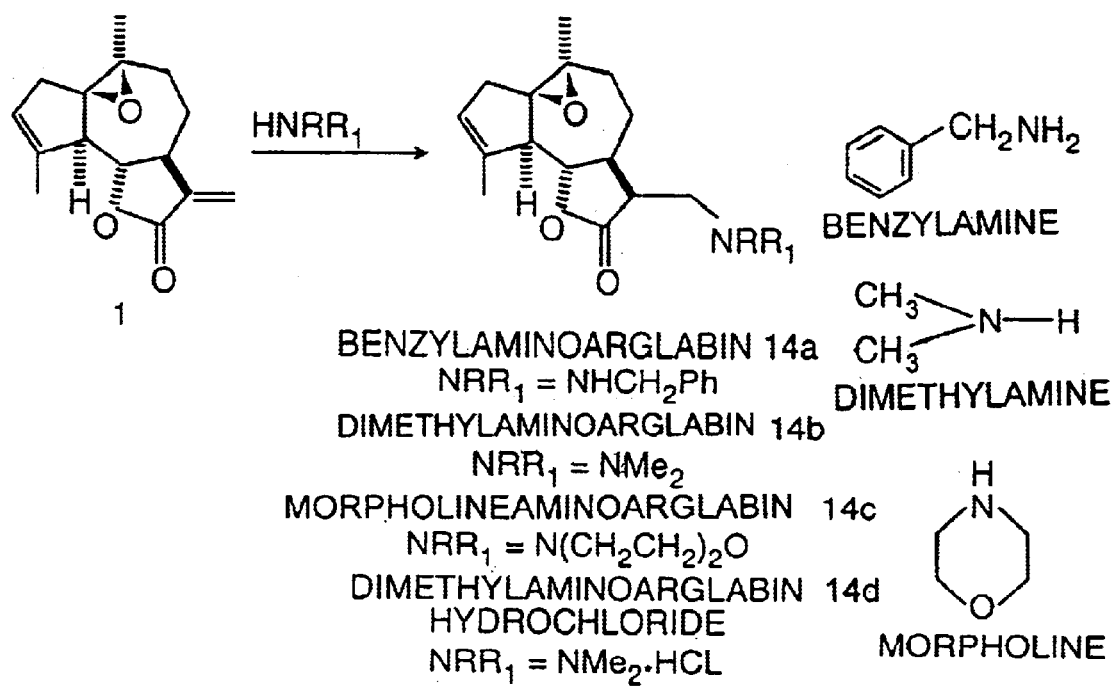
FIG. 3 depicts the synthesis of arglabin derivatives 14a–14d, 15a–15d and 16.
Figure 3:
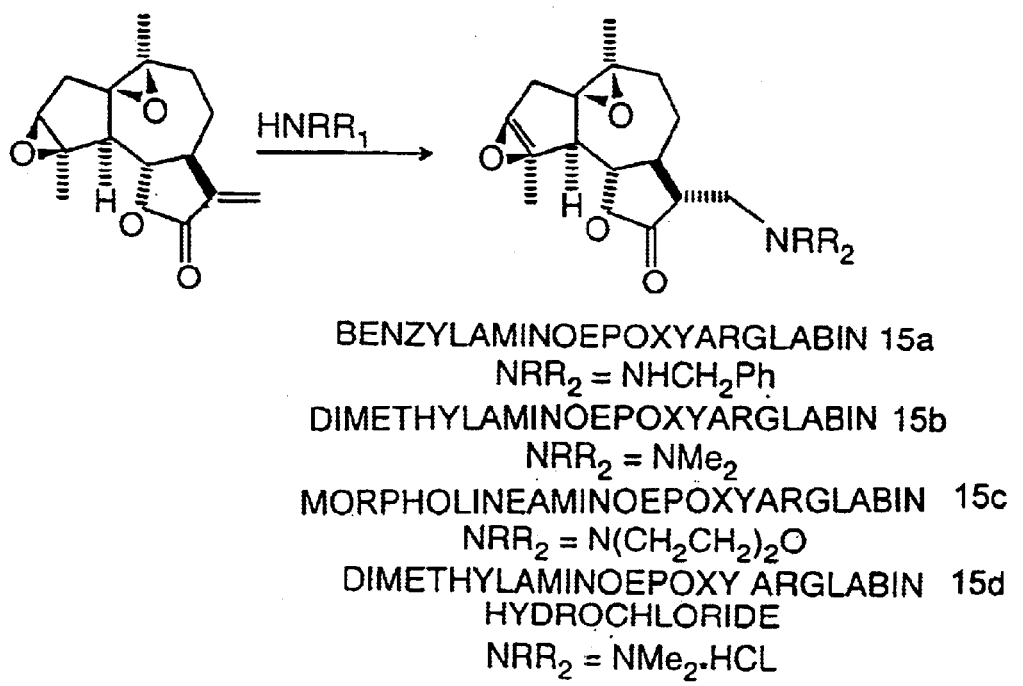
Figure 3:
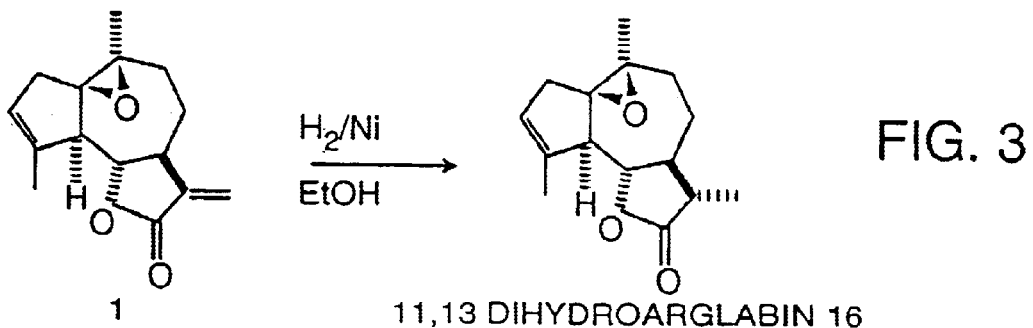

Interaction of arglabin 1 and epoxyarglabin 2 with benzeneamine, dimethylamine and morpholine in an alcohol medium proceeds chemoselectively as a Michael reaction on the activated double bond of these molecules, resulting in 56–856 of corresponding derivatives 14a-d and 15a-d (FIG. 3). The α configuration of the aminomethyl residue was proved spectrally.

Synthesis of dimethylaminoarglabin 14b: Arglabin 1 was mixed with 0.21 L of alcohol and heated to 40° C. until arglabin was fully dissolved. After filtering, a 33% solution of dimethylamine (0.023 L) was added dropwise with stirring. The mixture was left for 24 hours at room temperature. The reaction was monitored with TLC on silufol plates. After the amination reaction was complete, the mixture was heated to 52° C. and the alcohol was vacuum distilled. Approximately 0.63 L of chloroform was added to the remaining solvent and stirred for 30 minutes. The mixture was poured into a separatory funnel where the chloroform found in the lower part of the funnel was collected. The chloroform extraction was repeated two additional times with the aqueous layer. Magnesium sulfate was used to dry the collected chloroform. The chloroform-magnesium sulfate mixture was stirred for 30 minutes, then vacuum filtered to remove the chloroform. Approximately 22 g of dimethylaminoarglabin 14b was produced.

Dimethylaminoarglabin 14b was purified by first dissolving in 5 volumes (w/v) of chloroform then mixing with about 3 volumes (w/w) of KCK silica gel. After evaporation of the solvent, the dry material was chromatographically separated on a KCK silica gel column made with a 1:22 ratio of adduct to sorbent. The column was eluted by a mixture of petroleum diether and sulfuric ether (1:1, 1:2). Fractions of approximately 14–17 mls were collected and monitored with TLC. Dimethylaminoarglabin 14b was recrystallized from the fraction with chloroform and ether (1:1).

Summary of dimethylaminoarglabin 14b characteristics: melting point 94.5–95.5° C., [α]$^{21}{}_D$+47° (c 1.7, CHCl$_3$); elemental analysis 70.41% C, 8.7% H, 4.82% N (C$_{12}$H$_{25}$O$_3$N); IR (≧CHCl max) 3050–3000 (shoulder), 2940, 2860, 2835, 2780, 2410, 1770 (carbonyl lactone), 1650 (double bond), 1550–1530 (broad band), 1470, 1450, 1385, 1335, 1180, 1150, 1140, 1125 cm$^{-1}$ (epoxy group); MS (m/z, intensity in %) M+ HCl 291 (5.07, HCl), 247 (0.5), 188 (1,2), 115 (2,19), 105 (1,6), 97 (3,2), 77 (3,5), 70 (6,2), 67 (2,9), 58 (100); NMR (200 MHz, CDCl$_3$, δ scale; multiplety, P.P.M. KCCB) 1.90 (3H), 2.27 (6H), 4.00 (1H,) =9.5), broadened singlet 5.53 (1H), d.m. 2.66 (2H, J4=J2= 5.5).

Dimethylaminoarglabin hydrochloride 14d was produced by dissolving dimethylaminoarglabin 14b with 0.22 L of alcohol and heating to 40° C. After vacuum filtration, hydrogen chloride gas was produced by addition of 0.2 kg of sodium chloride and drops of concentrated sulfuric acid. The reaction was monitored by TLC. When the reaction was complete, the mixture was heated to 52° C. and the ethanol was vacuum distilled. Approximately 0.9 L of ethylacetate was added to the remaining tar with intensive stirring. The resulting precipitate yielded approximately 21 g of dimethylaminoarglabin hydrochloride 14d.

Approximately 0.1 L of chloroform was added to dissolve dimethylaminoarglabin hydrochloride 14d, then distilled to remove the chloroform. The remaining tar was mixed with 0.83 L of ethylacetate with intensive stirring. The mixture was cooled to insure complete precipitation of the product. The resulting precipitate was vacuum filtered to remove all solvent. The end product was vacuum dried over anhydrone and dissolved with apyretic distilled water at a ratio of 2 grams of dry material to 100 ml of water. Yield of dimethylaminoarglabin hydrochloride 14d was approximately 20 grams (95% of the estimated amount on this stage).

Summary of dimethylaminoarglabin hydrochloride 14d characteristics: melting point 203–204° C. (ethanol-ether); $[\alpha]^{21}_D +° 61.53°$ (c 0.52, $CHCl_3$); IR 33050–3000 (broad band), 2980, 2970 (intensive broad band, N—H); 2890, 2970, 2360–2300 (broad band), 1775 (carbonyl of lactone), 1650 (weak band), 1480, 1450, 1385, 1345, 1185, 1140–1120, 1100, 1065, 1040, 1010 $cm^{-1}$; MS (m/z, intensity in %) 291 (3.01, $M^+$ HCl), 115 (2.19), 105 (1.5), 97 (3.2), 91 (4.0), 77 (3.5), 70 (16.2), 67 (2.9), 58 (100); NMR (200 MHz, $CDCl_3$, δ-scale, multiplety, p.p.m. KCCB) c. 1.30 (3H), c. 1.87 (3H), c. 2.87 (6H), d.m. 4.17 (1H, J1=J2=10 Hz), broadened singlet 5.55 (1H).

11,13 dihydroarglabin 16 was produced by treating arglabin 1 with ethanol and $H_2$/Ni.

Example 3: Lyophilization

The water solution of dimethylaminoarglabin hydrochloride was filtered through a cotton-gauze plug or 8 layers of gauze, and a sterile Millipor filter to a sterile glass jar. The solution was vacuum pumped out of the jar into a measuring buret and aliquoted into 2 ml vials or ampules. The filled vials or ampules were maintained at −40° C. on sterile shelves for 24 hours prior to drying in a KC-30 lyophilizer or a LS-45 lyophilizer. After this tempering period, the drying process was started. The temperature was maintained at −40° C. for 2 hours, then was gradually increased to approximately 50° C. (plus or minus about 5° C.). The transition to approximately 500C occurred over about 12–13 hours of drying. The final temperature did not exceed +60° C. The total duration of drying time was 24 hours. After this, the vials with dry compound were immediately covered with caps and rolled. Ampules were soldered. Each vial or ampule contained about 0.04 g of the preparation.

Vials or ampules that were not sterile filtered were sterilized by autoclaving for 20 minutes at 120° C., with pressure of 1.2 Atm.

Alternatively, the prepared dimethylaminoarglabin hydrochloride water solution was filtered through a cotton-gauze plug or 8 layers of gauze. Approximately 200 ml of the solution were poured into 500 ml bottles, covered with cotton-gauze plugs and wrapped with oil-paper. The filled bottles were sterilized by autoclaving for 30 minutes at 120° C. with 1.2 Atm of pressure. The sterile solution was cooled to room temperature. Using sterile technique, 2 ml of the solution was poured into sterile 10 ml vials. The vials were then lyophilized as described above. After lyophilization each vial contained about 0.04 g of the compound.

Yield of the compound was 17 g, equaling 88.2% for this stage and 0.22% overall of dry natural material. The lyophilized material had a white-straw color and a bitter taste. Authenticity of the preparation was verified by determining its melting point and recording IR-, mass-, and NMR-spectra. The quality of the preparation was controlled by diluting 1 mg of the preparation with 0.2 ml of water. Addition of one drop of a saturated vanillin solution in concentrated sulfuric acid turned the mixture a violet color, indicating the presence of terpenes. Lyophilized material may be stored for three years.

Example 4: Isolation of Other Sespuiterene Lactones

Figure 4:
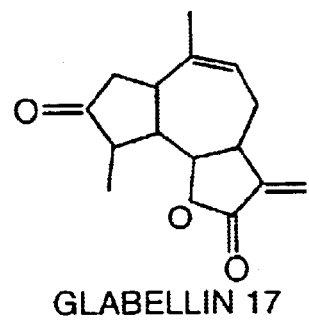
FIG. 4 depicts the structure of compounds 17 through 21.
Figure 4:
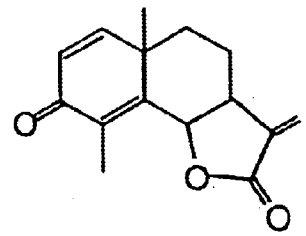
Figure 4:
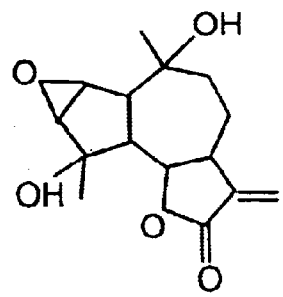
Figure 4:
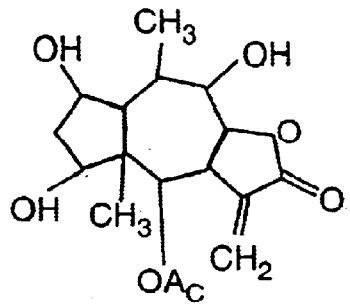

Structures for compounds 17 through 21 are shown in FIG. 4. Glabellin 17 was also isolated from *Artemisia glabella* Kar. et Kir. The yield of the compound from dry raw material was approximately 0.016%. The structure of glabella was determined through IR-, UN-, NMR, C13 NMR-, mass-spectra and chemical transitions.

Summary of Glabellin Characteristics: melting point 130–131° C. (petrol-diether); $[\alpha]^{20}_D +90.9°$ (SO, 17, chloroform).

3-keto-eudesm-1(2), 4(5), 11(13)-trien-6,12-olid(1) 18 was prepared by selective dehydration of α-sautonine with a yield of 45% and may be produced from more than 20 species of wormwood. The structure was determined by IR-, UV- and NMR-spectra.

Summary of 18 characteristics: melting point 145–147° C. (methanol); $[\alpha]^{18}_D -10.4°$ (with 1,12; chloroform).

Anobin 19 was extracted from *Achilles nobilis* L. The 2α,3α-epoxy-4α,10α-dioxy-5,7α(H), 6Oβ(H)-guai-11(13)-en-6,12-olide structure of anobin 19 was established by IR-, NMR- and mass-spectra and chemical transitions.

Epoxy estafiaton 20 was produced by isomerizing an available terpene lactone such as estafiatine through isomerization with etherate of trifluoride boron then epoxidizing with re-chlorbenzoil acid. The 3-keto-10α(14)-epoxy-1,5, 7α(H) 4,6β(H)-guai-11(13)-en-6,12-olid structure was determined by IR-, NMR- and mass-spectra.

Gaigranin 21 was produced by extraction of the aerial part of *Gaillardio grandiflora* with chloroform then chromatographically separating on a silica gel column. The structure of gaigranin 21 was confirmed by IR-, UV-, NMR and Cesy-spectra.

Example 5: In-vitro Activity of Arglabin and Derivatives—Viability of Cells

Transformed cells and primary cultures of normal cells were incubated with varying concentrations of dimethylaminoarglabin hydrochloride to determine its effect on the viability of the cells.

Mouse mastocytoma (P-815), myeloma (Z-P3x63Ag8.653 and Pai) and human erthyroleukemia (K-562) cell lines were used. Primary cultures of normal mouse hepatocytes were isolated from mouse liver using collagenase. Mouse splenocytes were isolated using a glass homogenizer. Marrow cells were obtained by washing the bone marrow. See, for example, Shears, S. B. and Kirk, C. J. (1984), *Biochem. J*. 219:375–382.

Figure 5:
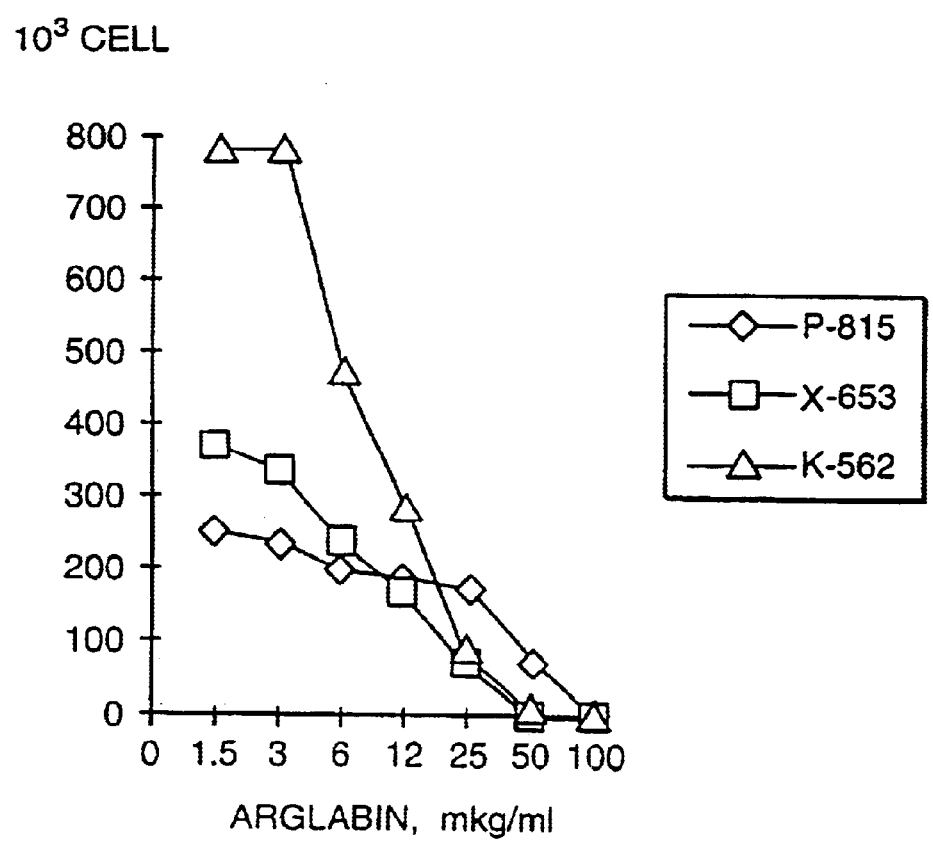
FIG. 5 depicts the effect of increasing concentrations of dimethylaminoarglabin hydrochloride on the viability of transformed cells.

Cells were cultured in RPMI-1640 medium supplemented with 10% fetal calf serum, 100 mM L-glutamine and 50

μg/ml gentamycin at 37° C. under 5% $CO_2$. Cells were seeded into 24-well plates at a density of 50,000 cells/well and grown until near confluency, approximately 2 days, then transferred to 96-well plates at the same density. Transformed cell lines were incubated for 18 hours with dimethylaminoarglabin hydrochloride, in concentrations ranging from 1.5 μg/ml to 100 μg/ml. Viability of the cells was determined by trypan blue exclusion. As shown in FIG. 5, a two fold reduction in viability was observed at 6 μg/ml for X-653 and K-562 cells and at 12 μg/ml for P-815 cells. Approximately 25% of K-562 and X-653 cells survived at a concentration of 12 μg/ml, and the same proportion of P-815 cells survived at a concentration of about 25 μg/ml. Higher concentrations of dimethylaminoarglabin hydrochloride further reduced the viability of all the transformed cells.

Figure 6:
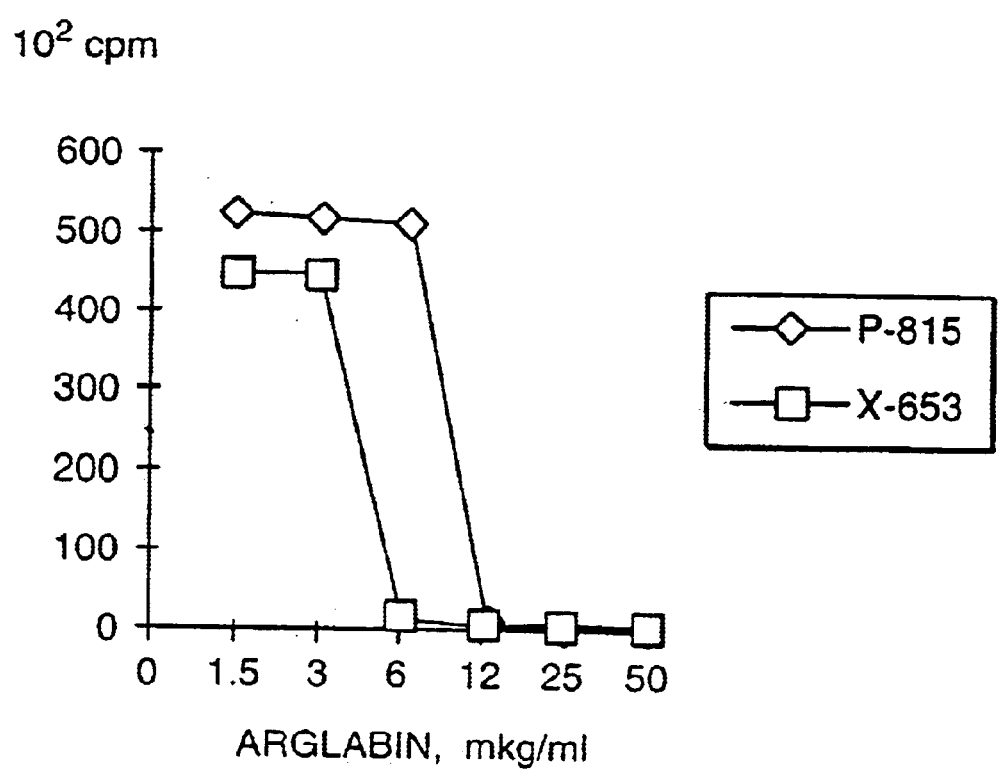
FIG. 6 depicts the effect of increasing concentrations of dimethylaminoarglabin hydrochloride on the proliferation of transformed cells.

The proliferation of the transformed cells was assessed by incubating $^3$H-labeled thymidine in the media for 18 hours. At the end of the specified time period, the proliferation was measured by counting the amount of $^3$H-thymidine incorporated. Thymidine incorporation provides a quantitative measure of the rate of DNA synthesis, which is typically directly proportional to the rate of cell division. FIG. 6 shows that proliferation of X-653 and P-815 cells was effectively blocked at concentrations of 6 μg/ml and 12 μg/ml, respectively.

Figure 7:
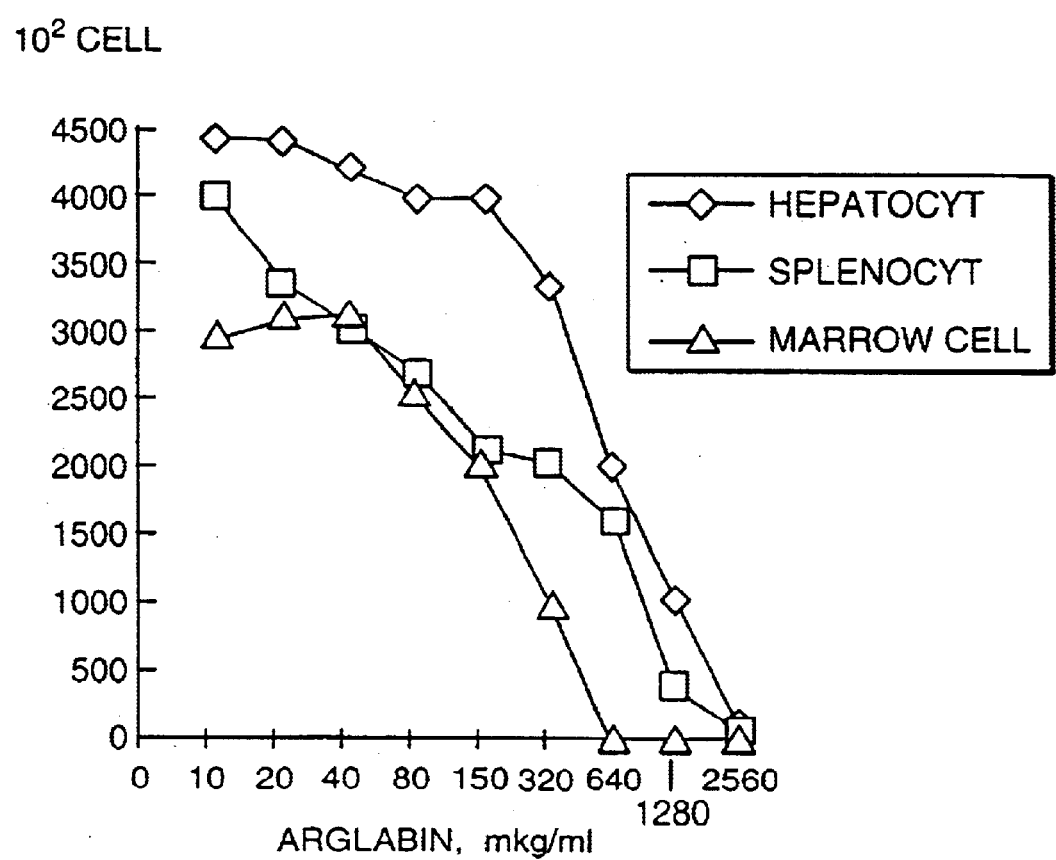
FIG. 7 depicts the effect of increasing concentrations of dimethylaminoarglabin hydrochloride on the viability of normal cells.

Primary cultures of normal cells were incubated for 18 hours with a concentration of dimethylaminoarglabin hydrochloride ranging from 10 μg/ml to 2560 μg/ml. Viability was measured by trypan blue exclusion. FIG. 7 shows that an increase in the concentration of dimethylaminoarglabin hydrochloride reduced the viability of the normal cells, but a much higher concentration was necessary to kill the normal cells, as compared to the transformed cells. At a concentration of 320 μg/ml, the number of viable splenocytes was reduced by 50% in comparison to the control. At concentrations of 640 μg/ml and 1280 μg/ml, 40% and 10%, respectively, of the splenocytes were still viable. At these same concentrations, approximately 50% and 25% of hepatocytes were still viable. Marrow cells were more sensitive to dimethylaminoarglabin hydrochloride. At a concentration of 160 μg/ml, only about 50% of the marrow cells were still viable. Increasing the concentration to 320 μg/ml reduced the viability to about 25%.

Protein Prenylation—Mouse myeloma Pai cells were cultured in the presence of 60 μM dimethylaminoarglabin hydrochloride. The cells were collected by centrifugation at 600×g for 10 minutes and then washed twice in PBS. Control cells were grown in the absence of drug. The cells were solubilized in lysis buffer (50 mM Tris, pH 7.4, 25 mM EDTA, 0.05% Tween, 0.01 M NaCl) for 30 minutes on ice. Lysates were made by homogenization for 5 minutes at 4° C. and precipitated by centrifugation at 12,000×g for 10 minutes. The supernatant was collected. Proteins were precipitated with trichloroacetic acid and then successively washed with ethanol and ethyl ether. A selective naphthol cleavage of the bond between isoprenoides and proteins was performed as described by Epstein, W. W et al., (1991) Proc. Natl. Acad. Sci. USA 88:9668–9670. In general, 5 mg of a potassium naphthoxide and naphthol 4:1 mixture was added to approximately 10 mg of precipitated protein. After addition of 50 μl of dimethylformamide, the tubes were gassed with argon, capped and heated to 100° C. for eight to 15 hours. Reaction products were extracted with hexane and analyzed by HPLC (Waters System) using a 0.4×15 cm reverse-phase Nova-Pac $C_{18}$ column. The column was eluted with 20% water in acetonitrile at a flow of 1.0 ml/minute. Napthol cleavage products were detected at 360 nm (FIG. 8) with a full-scale deflection of 0.01 A unit. In the control (FIG. 8A), the farnesylcysteine derivative eluted at 4.5 minutes and the geranylgeranylcysteine derivative at 6 minutes. The molar ratio of geranylgeranyl to farnesylcysteine was 6.

The influence of dimethylaminoarglabin hydrochloride on cellular prenylation is shown in FIG. 8B. Using 60 μM of dimethylaminoarglabin hydrochloride, the peak corresponding to the farnesylcysteine derivative does not appear on the chromatogram, while the geranylgeranyl peak appeared as in the control. This indicates that dimethylaminoarglabin hydrochloride can prevent farnesylation of proteins without significant effects on geranylgeranylation.

Example 6: In-vivo Activity of Arclabin and Derivatives

Overall, the compounds in this family have low toxicity and are tolerated at dosages exceeding the therapeutic dosage. Conventional toxicology methods were used to determine the $LD_{50}$ for an intraperitoneal injection of a 2% solution of dimethylaminoarglabin hydrochloride in dimethylsulfoxide (DMSO) in mice (weight 20–22 g) and rats (120–130 g). The $LD_{50}$ was 190–220 mg/kg in mice and 280–310 mg/kg in rats. An autopsy of the animals revealed plethoricy of internal organs, vasodilatation of the mesentery and intestines.

Tolerant single doses in rats and rabbits did not disturb the function of the liver, kidneys, cardiovascular system, respiration or peripheral nervous system. Blood pressure was maintained. In addition, no pyrogenic, allergenic, teratogenic or embryo toxic effects were observed in animals.

Maximum tolerable doses (MTD) of arglabin and derivatives were determined by daily intraperitoneal administration to rats, guinea pigs or mice and daily intravenous administration to rabbits over a period of five to 20 days. In general, the MTD ranged from about 20 mg/kg to about 50 mg/kg for all compounds tested. For example, the maximum dosage of dimethylaminoarglabin hydrochloride in a solution of DMSO ranged from 20 mg/kg in rabbits, 30 mg/kg in mice, 45 mg/kg in guinea pigs to 50 mg/kg in rats. Reversible changes in glycolysis and tissue respiration were observed in blood serum and hepatic tissue, changes of hormonal balance and elevation of protein in urine were observed after prolonged daily intraperitoneal administration of a 2% aqueous solution of dimethylaminoarglabin hydrochloride.

Inhibition of Tumor Growth in Rats—Human tumors were implanted into mice and rats (sarcoma M-1; Lymphosarcoma of Pliss; carcinosarcoma of worker; carcinoma of Geren; Sarcoma 45; Sarcoma 180; Sarcoma 37; Alveolar Cancer of liver PC-1; solid adenocarcinoma of Erlich; breast cancer (PMK); Lymphocytic leukemia P-388; lymphoidleukemia L-1210; variants of lymphosarcoma of Pliss resistant to rubidomycin, prospidine and leukoeffdine; and variants of sarcoma 45 resistant to sarcolysin, 5-fluorouracil, prospidine, and rubidomycin). Treatment was started 24 hours after implantation in mice and from the time measurable tumor nodes were detected in rats. Animals for the controls were formed into groups of 10–15. For estimating the anti-tumor activity of the compound, the percent tumor growth inhibition was determined after the end of treatment. The results were statistically analyzed using the t-test. Histologically, regression of the tumors was accompanied by dystrophy, necrosis of tumor cells, disturbance of blood supply to tumor tissue, and replacement with connective tissue.

Tables III and IV summarize the percent tumor growth inhibition activities of arglabin and various derivatives against both non-drug resistant and resistant tumors. For comparison, Table III also contains the percent tumor growth inhibition for colchicine, a compound with known anti-tumor activity. Introduction of haloids such as bromine and chlorine appears to increase the anti-tumor activity. Epoxidation of arglabin on the C3–C4 double bond also increases the anti-tumor activity. Dimethylaminoarglabin and dimethylaminoarglabin hydrochloride were effective against a wide range of tumors. One advantage of dimethylaminoarglabin hydrochloride is that it is soluble in water.

TABLE III

Antitumor Activity of Arglabin and its Derivatives

| Name of Sesquiterpene Lactone | Dose mg/kg | Inhibition of Tumour Growth, % | | | | | | | | | | |
|---|---|---|---|---|---|---|---|---|---|---|---|---|
| | | Pliss lympho-sarcoma | Worker's carcino-sarcoma | Geren's carcino-sarcoma | Sarcoma-45 | Sarcoma-37 | M-1 Sarcoma | Breast Cancer RMC-1 | Alveolar Cancer of the liver | Leukemia P-388 PALT | PC-1 | L-1210 |
| Arglabin (1) | 30 | 57.6 | 41.1 | 48.0 | 23.0 | | 55.6 | | 32.1 | +43.0% in survival | 32.1 | +34.1% in surv. |
| 11,13-dihydro-arglabin (16) | 30 | 68.0 | 46.4 | 84.4 | 64.1 | | 65.5 | | 68.7 | | | |
| Epoxyarglabin (2) | 30 | 72.1 | 36.4 | | 88.8 | | 78.4 | 59.6 | 70.4 | | | |
| Dimethylamino-arglabin (14b) | 50 | 56.0 | 30.0 | 85.1 | 79.0 | | | | 42.0 | 80.1 | | |
| | 30 | 78.2 | 30.0 | | 85.1 | | 79.9 | | | | 62.1 | |
| Dimethylamino-epoxyarglabin (15b) | 50 | 64.6 | 43.1 | 31.4 | 58.1 | | | | 38.0 | 51.0 | | |
| Dibromoarglabin (5) | 50 | 51.0 | 17.1 | 90.0 | 74.2 | | | | 69.0 | 46.9 | | |
| Arglabin chlorhydrin (6) | 50 | 49.1 | 38.4 | 43.1 | 21.0 | | | | 31.0 | 20.4 | | |
| Dichlordihydroxy-arglabin (3) | 50 | 29.0 | 63.2 | 71.4 | 70.9 | | | | 51.0 | 92.1 | | |
| Dimethylamino-arglabin hydro-chloride (14d) | 50 | 52.0–80.4* | 76.1–83.3** | 83.3* | 83.1** | | | | 80.0 | +109.0% in survival | | |
| | 30 | 79.6 | 76.1–80.1*** | 80.1 | 86.5*** | 78.2* | 83.5** | | | +144% in survival | 84.3* | +60% surv. |
| Dimethylamino-epoxyarglabin hydrochloride (15d) | 50 | 47.0 | 51.4 | 15.6 | 32.4 | | | | 29.1 | 31.2 | | |
| Anobin (19) | 20–30 | 60.0 | | 85 | | | | | | | | |
| Colchicine | 2 | 54.4 | 30.1 | 32.4 | 23.4 | 36.7 | 14.9 | | 29.1 | 31.2 | | |

*$p < 0.05$,
**$p < 0.01$,
***$p < 0.001$

TABLE IV

Antitumor Activity and Toxicity of Arglabin and its Derivatives

| Name of Sesquiterpene Lactone | Dose mg/kg | Inhibition of Tumour Strains Growth, % Resistant Forms | | | | | | |
|---|---|---|---|---|---|---|---|---|
| | | Sarcoma-45 | | | | Pliss Lymphosarcoma | | |
| | | to 5-fluorouracil | to sarcolysin | to prospidine | to rubidomycin | to rubidomycin | to prospidine | to leucoeffdine |
| Arglabin (1) | 30 | | 59.7 | | | 44.1 | 31.0 | |
| 11,13-dihydroarglabin (16) | 30 | | | | | | | |
| Epoxyarglabin (2) | 30 | 66.0 | | 70.4 | 78.6 | 78.0 | | 79.8 |
| Dimethylaminoarglabin (14b) | 50 | 52.1 | | | | | | |
| | 30 | | | | | | 52.1 | |
| Dimethylaminoepoxy-arglabin (15b) | 50 | 11.2 | | | | | | |
| Dibromoarglabin (5) | 50 | 46.3 | | | | | | |
| Arglabin chlorhydrin (6) | 50 | 15.2 | | | | | | |
| Dichlordihydroxyarglabin (3) | 50 | 70.6 | | | | | | |
| Dimethylaminoarglabin hydrochloride (14d) | 50 | 62.3 | 90.1*** | 87.4*** | | | 87.4*** | |
| | 30 | | | | | | 62.3 | |
| Dimethylaminoepoxy-arglabin hydrochloride (15d) | 50 | 13.2 | | | | | | |
| Anobin (19) | 20–30 | 13.2 | | | | | 95 | |

***$p < 0.001$

Combination Therapy—Results of the animal trials permitted design of the most rational scheme of treatment with dimethylaminoarglabin hydrochloride and other antitumor drugs.

A complete disappearance of tumors resistant to prospidin and rubidomycin was observed in 60% of rats treated with the combination of dimethylaminoarglabin hydrochloride, cisplatin and methotrexate. In addition, this combination overcame the cross-resistance of sarcoma-45 to methotrexate, sarcoma-45 to 5-Fluorouracil, and Pliss' lymphosarcoma to rubidomycin. No animals deaths were observed with this treatment.

The collateral sensitivity of leukofedin resistant Pliss' lymphosarcoma after administration of sarcolysin was accompanied by the complete disappearance of the tumor in 60% of the rats. The combination of dimethylaminoarglabin hydrochloride and sarcolysin, at half of the MTD, caused a block in DNA synthesis (synthesis inhibition index 94.1–97.1%). This combination did not decrease the blood cell level.

The combination of dimethylaminoarglabin hydrochloride and methylnitrosourea was administered at intervals of 2, 4 or 24 hours between the two drugs. It was determined that it was optimal to administer dimethylaminoarglabin hydrochloride two hours prior to administration of methylnitrosourea. The cross resistance of sarcoma-45 to prospidin and sarcoma-45 to 5-fluorouracil, Pliss' lymphosarcoma to rubidomycin and Pliss' lymphosarcoma to-prospidin was overcome with the combination of dimethylaminoarglabin hydrochloride and methylnitrosourea. Approximately 60% of the tumors disappeared in the rats without adverse drug reactions. Administration of methylnitrosourea prior to administration of dimethylaminoarglabin hydrochloride decreased the antitumor activity and increased toxicity.

Histologically, fewer small pyknotic polymorphic cells without clear structure were seen after treatment with the combination dimethylaminoarglabin hydrochloride and methylnitrosourea in comparison to the control group. It was found that dimethylaminoarglabin hydrochloride administered 2 hours prior to methylnitrosourea reduced toxicity.

The same results were seen when dimethylaminoarglabin hydrochloride was administered two hours prior to a mixture of vincristine and vinblastine for Geren's carcinoma and for Worker's carcinosarcoma.

Dimethylaminoarglabin hydrochloride moderately increased the duration of life in the animals with non-resistant and drug resistant tumors. The combination of dimethylaminoarglabin hydrochloride and other antitumor drugs further prolonged the duration of life. For example, the combination of dimethylaminoarglabin hydrochloride and vincristine prolonged life 114% in animals with methylnitrosourea resistant tumors. The combination of dimethylaminoarglabin hydrochloride and cisplatin, at half of MTD, prolonged life 117% in animals with methotrexate resistant L1210. A good therapeutic effect was seen from the triple combination of dimethylaminoarglabin hydrochloride, vincristine and cyclophosphamide at half of MTD as compared with the double combination of dimethylaminoarglabin hydrochloride and vincristine or dimethylaminoarglabin hydrochloride and cyclophosphamide. The triple combination prolonged duration of life by 209%. The quadruple combination of dimethylaminoarglabin hydrochloride, vincristine, cyclophosphamide and cisplatin was less effective than the triple combination. This may be due to increased toxicity of the antitumor drugs.

The effect of dimethylaminoarglabin hydrochloride alone and in combination with other drugs was studied in the model of drug resistant metastasis of Pliss' lymphosarcoma. The metastases in the inguinal lymphoid nodes were the most sensitive among the initial and drug resistant nodes. They did not develop in 10% of the cases. The duration of life for dimethylaminoarglabin hydrochloride alone was 128% in comparison with the control group. The combination of dimethylaminoarglabin hydrochloride and vincristine caused inhibition of tumor growth, with tumor dissolution, in 30% of the rats. Duration of life was increased 174% with the absence of any new metastases in the inguinal lymphoid nodes.

The combination of dimethylaminoarglabin hydrochloride and methotrexate prolonged the duration of life 300% in animals with prospidin resistant Pliss' lymphosarcoma. This combination led to an eight-fold decrease in the frequency of metastasis.

In order to reveal the possible mechanisms of dimethylaminoarglabin hydrochloride action against the initial and drug resistant tumors and their metastases, dimethylaminoarglabin hydrochloride and sarcolysin, alone and in combination, were used for the treatment of sarcoma 45 to investigate the disturbance of DNA synthesis. Beneficial results were observed with sarcolysin and with the combination of sarcolysin and dimethylaminoarglabin hydrochloride in the case of the non-drug resistant sarcoma 45. In the case of drug resistant sarcoma 45, dimethylaminoarglabin hydrochloride alone was very effective (DNA inhibition index 99%). Moreover, DNA inhibition increased after 24 hours upon daily administration over the subsequent 5 and 10 days. This indicated that repeated administration of dimethylaminoarglabin hydrochloride, rather than a single administration of the MTD, had a cumulative antitumor effect.

The immunity of rats with initial and prospidin resistant tumors with metastases was studied after treatment with dimethylaminoarglabin hydrochloride alone and in combination with other cytostatics. An improvement of the immunodepression found after treatment with sarcolysin and cisplatin was observed after treatment of the animal tumors with dimethylaminoarglabin hydrochloride. The combination of dimethylaminoarglabin hydrochloride and sarcolysin or cisplatin increased immunological indices, particularly if dimethylaminoarglabin hydrochloride was administered two hours before the cytostatic drugs. These results suggested that dimethylaminoarglabin hydrochloride softened the immunodepressive effect of cytostatics and normalized the immune balance of the body. These data show that dimethylaminoarglabin hydrochloride decreased cytotoxicity and increased the efficacy against drug resistant tumors alone and in combination.

Immune System Modulation—The effect of dimethylaminoarglabin hydrochloride was determined in intact and immunodepressed mice. Mice were immunodepressed by administration of 200 mg/kg of cyclophosphamide. Injection of cyclophosphamide resulted in considerable leukopenia related primarily to lymphopenia. The humoral immunity of the animals was considerably suppressed, as was cell-mediated immunity although to a lesser extent. Two dosages of a 2% dimethylaminoarglabin hydrochloride solution, 50 and 100 mg/kg, were injected IP into white mongrel mice. The Hemagglutination test and delayed-type hypersensitivity reaction were determined before and after administration of drug. It was determined that a single 50 mg/kg dosage of dimethylaminoarglabin hydrochloride did not alter the hemagglutination titer or the delayed-type hypersensitivity reaction. Dosages of 100 mg/kg resulted in a slight decrease in hemagglutination titer.

Repeated IP injections of 10 to 50 mg/kg dimethylaminoarglabin hydrochloride were administered over five to 10 days to determine the effect of prolonged administration. It was found that lower dosages such as 10 and 20 mg/kg, increased hemagglutination titers by days 5 and 10. Administration of higher dosages, such as 30 mg/kg, resulted in a decreased hemagglutination test index by day 10. No effect on delayed-type hypersensitivity reaction was seen at day 5, but was increased by day 10.

In intact mice, injection of 10 mg/kg increased the total number of leukocytes through an increase in the absolute number of lymphocytes. The relative number of neutrophils was slightly reduced. Increasing the dosage to 20 mg/kg did not result in an overall increase in leukocyte number. The nitroblue tetrazolium assay was used to assess the function of the neutrophils. It was found that while the number of neutrophils was decreased, activity of the neutrophils was not altered at 10 mg/kg. With a higher dosage, 20 mg/kg, a decrease in nitroblue tetrazolium positive neutrophils was seen, indicating a decrease in function.

Daily IP administration of 10 and 20 mg/kg dimethylaminoarglabin hydrochloride for 10 days to intact mice resulted in a dramatic change in T-lymphocytes, B-lymphocytes and natural killer cells. At 10 mg/kg, the overall leukocyte count was increased through an increase in natural killer cells and T-lymphocytes while B-lymphocytes remained stable. It was found that the increase in T-lymphocyte number was a result of an increase in the level of the T-helper subpopulation. The level of the T-suppressor subpopulation was not altered. At a higher dosage (20 mg/kg), overall leukocyte number was not altered, even though B-lymphocyte number decreased and T-lymphocyte decreased to a lesser extent. Natural killer cell number was increased. The nitroblue-tetrazolium assay was also decreased.

Overall, the effect of dimethylaminoarglabin hydrochloride on the immune system depended on the administrated dose. At a low dosage (10 mg/kg), dimethylaminoarglabin hydrochloride increased T and B-lymphocytes and natural killer cell levels. The increase in T-lymphocytes was accompanied by an increase in the level of the T-helper subpopulation of T-lymphocytes. Higher dosages of dimethylaminoarglabin hydrochloride (20 mg/kg) decreased T and B-lymphocyte number, but increased certain other cell populations, such as natural killer cells.

Injection of 10 mg/kg dimethylaminoarglabin hydrochloride to immunodepressed mice for 10 days reduced the leukopenia and lymphopenia observed in the mice. By the tenth day of treatment, the total number of lymphocytes in immunodepressed animals did not differ from the values obtained from intact animals. The increased number of T-lymphocytes was accompanied by an elevation in the T-helper subpopulation as well as the T-suppressor subpopulation, although to a lesser extent. The numbers of B-lymphocytes were not completely restored to normal values.

Additional immunological data were obtained from an "August" line of rats, weighing 140–160 g, with and without Pliss lymphosarcoma. Four indices, spontaneous rosette forming of erythrocytes, nitroblue tetrazolium assay, delayed-type hypersensitivity and hemagglutination were examined before treatment, during treatment (5 and 10 days) and 5 days after treatment with dimethylaminoarglabin hydrochloride. Approximately 50 mg/kg of a 2% water solution of lyophilized-dimethylaminoarglabin hydrochloride was injected IP, daily, for 10 days. Results are summarized in Table V. Overall, lyophilized-dimethylaminoarglabin hydrochloride stimulated delayed type hypersensitivity, but reduced all other studied indices in intact rats. In rats with Pliss Lymphosarcoma, the immune system was stimulated, as all studied indices increased. An advantage of lyophilized-dimethylaminoarglabin hydrochloride is that it ameliorates the immunodepressive effect of known cytostatics such as 5-fluorouracil and sarcolysin.

TABLE V

| INDEX | Intact Rats After Treatment | Rats with Pliss Lymphosarcoma After Treatment |
|---|---|---|
| Spontaneous-erythrocyte rosette forming (E-ROK) | Decreased 64–84% | Increased 94.8–162.5% |
| Nitroblue tetrazolium (NBT) | Decreased 67–91% | Increased 79.2–175.4% |
| Delayed type hypersensitivity | Increased 153–207% | Increased 89.9–132.2% |
| Hemagglutination (RHG) | Decreased 43–53% | Increased 82.2–142.6% |

Pharmacokinetics—Experimental pharmacokinetic data were obtained for dimethylaminoarglabin hydrochloride using 30 random bred rats of both sexes. The rats weighed from 200–220 grams. Gas chromatography and a FARM modelling program was used in the analysis of all pharmacokinetic data. Intravenous 2 mg/kg dimethylaminoarglabin hydrochloride showed a maximal level of 30 $\mu$g/ml in the blood serum within one hour. Dimethylaminoarglabin hydrochloride spread quickly throughout the organism from the blood to peripheral tissues. The obvious volume of distribution was large, indicating that it could pass through cell membranes and tissue barriers. The highest concentration of drug was accumulated in the lungs and spleen during the first hour after administration. Maximum lung and spleen concentrations were 149.4 and 159 $\mu$g/g, respectively. Within three hours after administration, the concentration in the liver and skeletal muscle was 228.6 and 176.4 $\mu$g/g, respectively. It was found that the preparation accumulated in the liver and was retained for a more extended period in comparison to other tissues. Dimethylaminoarglabin hydrochloride was able to penetrate through the blood-brain barrier. Brain tissue concentration was 23.9 $\mu$g/g after one hour and stabilized at 15.6 $\mu$g/g in 24 hours.

Dimethylaminoarglabin hydrochloride was excreted fairly slowly. The biological half-life was about 46.8 hours in rats, with the average time-of retention about 67 hours. Renal excretion proceeded slowly. The kidney concentration was maximal after three hours. By 24 hours, the kidneys had the highest concentration, 56.6 $\mu$g/g. Total clearance was 0.5 ml/minute at a low transportation rate of the preparation from peripheral tissues into the blood.

Clinical Data on Dimethylaminoarglabin Hydrochloride

A first clinical trial of dimethylaminoarglabin hydrochloride was performed on 51 patients with end-stage (III–IV) cancer. 20.7% of the patients in the first clinical trial had lung cancer, 17% had liver cancer, 17% had stomach cancer, 9.4% had rectal cancer, 5.7% had ovarian cancer, 5.7% had esophageal cancer, and the remaining had either salivary gland, lymphosarcoma, breast or large intestinal cancer. The patient population was 67.9% male and 32.1% female. Generally, patients were intravenously given reconstituted dimethylaminoarglabin hydrochloride in an aqueous solution. In patients with ascites, dimethylaminoarglabin hydrochloride was administered intraperitoneally. Intrapleural administration was used for patients with pleurisy. Patients were given a very small dose and monitored for any signs of allergic reaction before proceeding. Initially, 80 mg of the compound was given per day as a single dose, then gradually increased to a maximum level. After 30–35 days, the dose was increased to 480 mg per day. At this high dose, patients complained of nausea and vomiting. It was estimated that the daily dose should be about 240–280 mg for typical cases. Total dose over the course of treatment was typically five to six grams of dimethylaminoarglabin hydrochloride, but was as high as 20 grams. Immediately after administration of the compound, patients reported a bitter taste that quickly dissipated. Additional courses of treatment were administered to some patients. A summary of the data from the first clinical trial is shown in Table VI. Patient condition before treatment was rated on a scale of 1 to 3, where 1 was bedridden, 2 was a significant restriction on activity and 3 retained full activity. Therapeutic result was measured on a scale from 0 to 3, where 0 was no improvement, 1 was insignificant or improvement for less than a month, 2 was considerable improvement (25–50% reduction in tumor size) and 3 was sharp improvement (50–100% reduction in tumor size).

TABLE 6

Karaganda Region Oncological Centre Clinical Data from Patients Treated with Dimethylaminoarglabin Hydrochloride During I and II Phases of Studying

| N | Age | Sex M/F | Case Number | Diagnosis | General Condition Before Treatment | TNM* | Administration | Prevalent Single dose (mg) | Total Cumulative Dose (mg) | Duration of Treatment (Days) | Initial and Minimal Amount of Leukocytes of Thrombocytes | Side Effects | Therapeutic Result** Objective | Therapeutic Result** Subjective | Note(s) |
|---|-----|-----|---------|-----------|-----------------------------------|------|----------------|----------------------------|----------------------------|------------------------------|---------------------------------------------------------|-------------|-------------------------------|--------------------------------|---------|
| 1 | 41 | M | 631/93 | Cancer of the submaxillary salivary gland III stage | 3 Satisfactory | T-3 N-0 M-0 | IV | 30–240 | 6000 | 31 | L-5.6 Tr-2.7 | No | 0 | 0 | |
| 2 | 34 | M | 660/93 | Lymphosarcoma of the lymphatic nodes III stage | 3 Medium level of gravity | | IV | 200–240 | 4200 | 14 22 | L-4.0 Tr-2.73 | No | 0 | 0 | |
| 3 | | M | | Carcinoma of the stomach. State after the gastrectomy. Ascites. IV stage | 1 | | IP | 280 | 1960 | 7 | L-6.5 Tr-3.4 | No | 1 | 1 | |
| 4 | | M | | Cancer of the left lung. Exudative pleurisy IV stage. N2309-C | 1 | | IV I. Pleural | 120 240 | 1320 2400 | 25 | L-6.3 Tr-2.25 | No | 1 | 1 | |
| 5 | 61 | M | 130/93 | Carcinoma of the stomach IV stage. Metastasis to the liver. Ascites. | 2 | T-3 N-x M-t | IV | 80–120 | 2400 (600 mg 1st course) | 30 18 | L-10 Tr-1.5 | No | 0 | 1 | 2 courses |
| 6 | 37 | M | 276/93 | Lymphoblative lymphosarcoma of the lymphatic nodes | 2 | | IV I. Pleural | 240 400 | 7000 400 | 7 1 | L-7.3 Tr-1.9 | No | 0 | 0 | Polychemotherapy - cyclophosph 1000 + rubomycin 86 3 courses |
| 7 | 71 | M | 1768/93 | Carcinoma of the stomach IV stage. MTS to the liver. | 2 Near satisfactory | T-4 N-x M-t | IV | 240–280 | 4920 (2720 mg 1st course) | 17 | L-7.3 Tr-2.8 | Hemorrhage from the tumour | 0 | 1 | |
| 8 | 64 | F | 788/93 | Cancer of the ovary III stage. Ascites. N2279-85. | 3 Satisfactory | T-3 N-1 M-o | IV | 280 | 3820 (40 mg 1st course) | 15 | L-3.5 Tr-2.8 | abs | 2 | 2 | |
| 9 | 50 | F | 2006/93 | Plural cancer of the gastrointestinal tract | 2 Complicated | | IV | 240–360 | 16500 (8800 mg 1st course) | 45 | L-4.7 Tr-1.8 | abs | 1 | 2 | 2 courses - polychemotherapy - arglabin + methotrexate 4000 mg |
| 10 | 67 | M | 2134/93 | Carcinoma of the liver IV stage. Colexia. | 3 Medium gravity | T-2 N-x M-t | IV | 240–480 | 17450 (8690 mg 1st course) | 52 | L-5.3 Tr-2.78 | Bitterness in the mouth, smell of the absinthium, nausea | 1 | 2 | 3 courses - polychemotherapy - arglabin + fluorovital 3750 mg |
| 11 | 35 | M | 1362/93 | Cancer of the rectum. MTS into the liver. N82-96. | 3 Satisfactory | T-4 N-2 M-0 | IV | 220–240 | 4800 | 10 | L-4.5 Tr-2.2 | Bitterness in the mouth, nausea | 1 | 1 treatment | Refused further |

TABLE 6-continued

Karaganda Region Oncological Centre Clinical Data from Patients Treated with Dimethylaminoarglabin Hydrochloride During I and II Phases of Studying

| N | Age | Sex M/F | Case Number | Diagnosis | TNM* | General Condition Before Treatment | Administration | Prevalent Single dose (mg) | Total Cumulative Dose (mg) | Duration of Treatment (Days) | Initial and Minimal Amount of Leukocytes of Thrombocytes | Side Effects | Therapeutic Result** Objective | Subjective | Note(s) |
|---|---|---|---|---|---|---|---|---|---|---|---|---|---|---|---|
| 12 | 48 | F | 1400/93 | Cancer of the ovary IV stage. Ascites. MTS to the liver. NSS. | T-4 N-2 M-t | 3 Satisfactory | IP | 240–320 320–400 | 4000 3800 | 29 | L-9.9 Tr-2.13 | No | 1 | 2 | Polychemotherapy - cyclophosphamide (IV 2800 mg) methotrexate (120 mg) fluoruracil (2000 mg) + arglabin |
| 13 | 63 | F | 2136/93 | Carcinoma of the liver IV stage. MTS into the liver. N572-c. | 3 | 3 | IV | 320–360 | 17560 | 56 | L-3.3 Tr-2.0 | No | 2 | 2 | 3 courses |
| 14 | 63 | M | 2136/93 | Carcinoma of the liver IV stage. MTS into the liver N1048-c. | T-3 N-x M-t | 3 Medium gravity | IV | 240–320 | 19770 (19400 mg 1st course) | 26 | L-4.7 Tr-2.6 | No | 2 | 2 | |
| 15 | 70 | M | 2056/93 | Cancer of the right lung IV stage. | T-3 N-2 M-1 | 1 Medium gravity | I. Pleural | 320–400 | 6600 20000 | 6 31 | L-12.3 Tr-2.6 | No | 1 | 1 | |
| 16 | | F | 2235 | Primary carcinoma of the liver | | 2 Grave | IV | 120–160 | 4440 (2040 mg 1st course) | 32 | L-10.0 Tr-1.8 | No | 2 | 3 | 2 courses |
| 17 | 73 | M | 3671/93 | Carcinoma of the liver III stage. Ascites. | T-3 N-x M-o | 1 Medium grave | IV IP | 240–280 400 | 5600 4400 | 20 | L-5.7 Tr-2.7 | No | 2 | 1 | |
| 18 | 54 | M | 3351/93 | Carcinoma of the stomach IV stage. MTS into the retroperitoneal lymphatic nodes. N448-50. | T-4 N-x M-t | 2 | IV | 280 | 4600 | 15 | L-5.4 Tr-2.42 | No | 1 | 2 | |
| 19 | 72 | M | 1940/93 | Plural cancer of the body-skin II stage. N5881-5. | T-3 N-0 M-0 | 3 | External | 0.04 | 40 | 10 | L-7.8 Tr-2.9 | Allergy itch in the rectum | 0 | 0 | |
| 20 | 45 | M | 3583/93 | Cancer of the left lung IV stage. MTS into the lymphatic nodes of the mediastinum. | T-3 N-2 M-1 | 1 Medium grave | IV | 240 | 3600 | 16 | L-3.5 Tr-2.28 | No | 2 | 2 | 2 courses |
| 21 | 64 | M | 3131/93 | Carcinoma of the stomach. MTS into the liver. Ascites. Pleurisy. | T-3 N-x M-o | 1 grave | IV | 240 | 2400 | 10 | L-5.2 Tr-2.0 | No | 0 | 0 | |

TABLE 6-continued

Karaganda Region Oncological Centre Clinical Data from Patients Treated with Dimethylaminoarglabin Hydrochloride During I and II Phases of Studying

| N | Age | Sex M/F | Case Number | Diagnosis | General Condition Before Treatment | TNM* | Administration | Prevalent Single dose (mg) | Total Cumulative Dose (mg) | Duration of Treatment (Days) | Initial and Minimal Amount of Leukocytes of Thrombocytes | Side Effects | Therapeutic Result** Objective | Subjective | Note(s) |
|---|---|---|---|---|---|---|---|---|---|---|---|---|---|---|---|
| 22 | 18 | M | 3300/94 | Cancer of the rhinopharynx IV stage. MTS into the lymphatic nodes of the neck. N5133-7/4. | 1 | T-3 N-2 M-o | IV | 240 | 3600 | 15 | L-6.2 Tr-2.64 | No | 1 | 1 | Radiation treatment |
| 23 | 42 | M | 3449/93 | Cancer of the pancreas IV stage. | 2 Satisfactory | T-4 N-x M-t | IV | 240–400 | 8000 | 23 | L-4.8 Tr-2.5 | No | 1 | 1 | |
| 24 | 41 | F | 3854/93 | Cancer of the left breast. Secondary pleurisy of the left side IV stage. | 2 | T-2 N-2 M-0 | I. Pleural | 800–1000 | 5000 (4000 mg 1st course) | 6 | L-4.5 Tr-3.0 | No | 1 | 1 | Polychemotherapy (Fluoruracil I. Pleural, 1000 mg) + arglabin |
| 25 | 55 | F | 4984/93 | Cancer of the right lung with exudative pleurisy IV stage. M4164-c. | 3 Satisfactory | T-2 N-x M-x | I. Pleural | 400 | 4000 | 10 | L-3.7 Tr-2.6 | No | 2 | 2 | 2 courses |
| 26 | 38 | F | 3504/93 | Cancer of the right lung. MTS into the supraclavicular l/n. IV stage. N12432-34. | 2 Medium gravity | T-3 N-3 M-0 | IV | 240–280 | 4400 | 17 | L-15.4 Tr-2.1 | No | 0 | 0 | |
| 27 | 65 | M | 2038/93 | Cancer of the rectum. Germination into the urinary bladder IV stage. | 2 Weak | T-3 N-2 M-t | Supp. | 2 supp. 3 × day | 180 supp | 25 | L-8.8 Tr-2.8 | No | 0 | 1 | Polychemotherapy - fluoruracil-IV, 5000 mg + arglabin |
| 28 | 68 | M | 4166/93 | Cancer of the large intestine. MTS into the retro peritoneum l/n. IV stage. N13471. | 3 | T-4 N-2 M-T | IV | 240 | 4800 | 20 | L-6.3 Tr-2.3 | No | 0 | 0 | Radiation (x-ray to left lung) |
| 29 | 62 | M | 4293/93 | Cancer of the left lung III stage. | 2 | T-3 N-2 M-0 | IV | 240 | 960 | 4 | L-5.6 Tr-3.1 | No | 0 | 0 | Radiation applied to left lung |
| 30 | 57 | M | 4319 | Cancer of the esophagus IV stage. N1418 | 3 | T-3 N-x M-1 | IV | 240 | 960 | 4 | L-3.7 Tr-2.6 | No | 0 | 0 | |

TABLE 6-continued

Karaganda Region Oncological Centre Clinical Data from Patients Treated with Dimethylaminoarglabin Hydrochloride During I and II Phases of Studying

| N | Age | Sex M/F | Case Number | Diagnosis | General Condition Before Treatment | TNM* | Administration | Prevalent Single dose (mg) | Total Cumulative Dose (mg) | Duration of Treatment (Days) | Initial and Minimal Amount of Leukocytes of Thrombocytes | Side Effects | Therapeutic Result** Objective | Subjective | Note(s) |
|---|---|---|---|---|---|---|---|---|---|---|---|---|---|---|---|
| 31 | 50 | M | 1466/93 | Corpus ventriculi cancer, infiltrate form III stage. Ascites. Colexia. | 2 | T-3 N-x M-o | IP | 360 | 3240 (720 mg 1st course) | 9 | L-5.6 Tr-3.84 | No | 0 | 0 | Polychemotherapy - fluoruracil, IV, 1680 mg + arglabin |
| 32 | 64 | F | 1703/93 | Cancer of the head of the pancreas. MTS into liver and lungs. Ascites. IV stage. | 2 | T-3 N-x M-t | IP | 320 | 2980 | 9 | L-6.1 Tr-2.3 | No | 1 | 1 | |
| 33 | | M | | Cancer of the rectum. MTS into the liver. IV stage. | 3 | | IV | 240–320 | 10640 | 38 | L-5.1 Tr-2.11 | No | 2 | 2 | |
| 34 | | M | | Cancer of the rectum. MTS into the liver. retroperitoneum lymphatic nodes. IV stage. N2203-c. | 2 | | IV | 240 | 3120 | 13 | L-7.4 Tr-3.4 | No | 0 | 1 | |
| 35 | | M | | Carcinoma of the stomach. IV stage. N9129-40. | 2 | | IV | 280–320 | 9040 | 30 | L-5.2 Tr-2.7 | No | 0 | 1 | 2 courses |
| 36 | 34 | F | 2390/93 | Carcinoma of the stomach. Crukenberg's MTS. N687-90. | 3 | T-3 N-1 M-1 | IV | 240 | 480 | 2 | L-4.0 Tr-2.8 | No | 1 | 0 | Polychemotherapy - fluoruracil - IV 4000 mg, arglabin - IV 480 mg, methotrexate - 60 mg enterally |
| 37 | 59 | M | 4606/94 | MTS into the DV, DXI vertebrae, liver without the primary focus. | 2 | T-x N-x M-1 | IV | 240 | 1240 1920 | 8 | L-7.0 Tr-2.4 | No | 0 | 0 | Radiation |
| 38 | 67 | M | 282/94 | Cancer of the left lung. III stage. | 3 | T-3 N-x M-0 | IV | 200 | 600 4080 | 3 | L-5.3 Tr-2.5 | No | 2 | 2 | 4 courses polychemotherapy - fluoruracil, IV - 1000 mg + arglabin |

TABLE 6-continued

Karaganda Region Oncological Centre Clinical Data from Patients Treated with Dimethylaminoarglabin Hydrochloride During I and II Phases of Studying

| N | Age | Sex M/F | Case Number | Diagnosis | General Condition Before Treatment TNM* | Administration | Prevalent Single dose (mg) | Total Cumulative Dose (mg) | Duration of Treatment (Days) | Initial and Minimal Amount of Leukocytes | of Thrombocytes | Side Effects | Therapeutic Result** Objective | Subjective | Note(s) |
|---|---|---|---|---|---|---|---|---|---|---|---|---|---|---|---|
| 39 | 40 | M | 372/94 | Cancer of the lower lobe of the left lung. III stage. Exudative pleurisy. N2112. | T-3 N-x M-0 3 | IV I. Pleural | 400 | 2800 3240 | 7 | L-4.2 Tr-2.7 | | No | 2 | 3 | Polychemotherapy therapy |
| 40 | 64 | M | 695/94 | Cancer of the superior lobe of the left lung. III stage. | T-3 N-x M-0 3 | IV | 240 | 7200 | 30 | L-6.2 Tr-2.6 | | No | 2 | 3 | |
| 41 | 62 | M | 625/94 | Cancer of the lower lobe of the right lung. IV stage. Exudative pleurisy. N402-c. | T-3 N-x M-x 3 | I. Pleural | 400 | 7600 (3600 mg 1st course) | 18 | L-4.6 Tr-2.8 | | No | 2 | 3 | |
| 42 | 50 | F | 2261/93 | Cancer of the ovariums. III stage. N7428-31. | T-3 N-0 M-0 3 | IP | 240 | 3360 | 14 | L-5.2 Tr-2.7 | | No | 2 | 2 | Partial regression |
| 43 | 53 | F | 972/94 | Primary cancer of the liver. III stage. N179-c. | T-3 N-x M-0 3 | IV | 240 | 5460 (4500 mg 2nd course) | 19 | L-6.3 Tr-2.0 | | No | 1 | 1 | 2 courses |
| 44 | | M | 859/94 | Cancer of the esophagus. MTS into the liver. | T-3 N-2 M-1 3 | IV | 240 | 4800 | 27 | L-3.3 Tr-3.0 | | No | 1 | 1 | Polychemotherapy - Methotrexate (150 mg IV), arglabin |
| 45 | 59 | M | 1571/94 | Primary tumor of the liver. | T-4 N-x M-0 3 | IV | 240 | 6240 | 27 | L-2.3 Tr-3.0 | | No | 1 | 2 | |
| 46 | 65 | F | 1131/93 | Liver cancer IV stage. | T-3 N-x M-t 3 | IV | 240 | 10000 9600 | 48 | L-4.2 Tr-2.8 | | No | 1 | 2 | 2 courses |
| 47 | 57 | M | 1236/94 | Rectal cancer III stage. | T-4 N-x M-0 3 | Supp. 2/3 × day | | 6720 | 23 | L-4.9 Tr-2.5 | | Aches and itch in rectum | 1 | 1 | 50% decrease in tumor |
| 48 | 66 | M | 564/94 | Liver tumor IV stage. Gastric cancer. | T-3 N-x M-1 3 | IV | 240 | 6720 | 28 | L-4.7 Tr-2.4 | | No | 1 | 0 | |
| 49 | | M | 1337/94 | Esophogal cancer III stage. | T-4 N-x M-0 2 | IV Enterally | 240 40 | 4800 720 | 24 18 | L-4.6 Tr-2.6 | | No | 1 | 1 | Radiation |

TABLE 6-continued

Karaganda Region Oncological Centre Clinical Data from Patients Treated with Dimethylaminoarglabin Hydrochloride During I and II Phases of Studying

| N | Age | Sex M/F | Case Number | Diagnosis | General Condition Before Treatment TNM* | Prevalent Single dose (mg) | Total Cumulative Dose (mg) | Duration of Treatment (Days) | Initial and Minimal Amount of Leukocytes | Side Effects | Therapeutic Result** Objective | Subjective | Note(s) |
|---|---|---|---|---|---|---|---|---|---|---|---|---|---|
| 50 | 55 | F | 1168/94 | Carcinoma of the stomach III stage. | T-3 3<br>N-x<br>M-0 | 240 | 3366 | 14 | L-4.7<br>Tr-2.8 | No | 1 | 0 | Refused further treatment |
| 51 | 53 | | 1110/94 | Cancer of the left lung III stage. | T-3 3<br>N-x<br>M-x | 240<br>40 | 3120<br>520 | 13<br>13 | L-8.6<br>Tr-3.0 | No | 2 | 1 | |

*T subclasses (Primary tumor),
Tx—tumor cannot be adequately assessed,
T0—no evidence of primary tumor,
TIS—carcinoma in situ, T1, T2, T3, T4 - progressive increase in tumor size and/or involvement
N (Regional lymph node),
Nx—regional lymph nodes cannot be assessed clinically,
N0—no evidence of regional node metastasis, N1, N2, N3 - increasing involvement of regional lymph nodes
M subclasses (Distant metastasis),
Mx—not assessed,
M0—no distant metastasis,
M1—distant metastasis present, specify site(s)

Overall, approximately 30% of the patients had a considerable improvement. 55.6% of patients with liver cancer had a considerable improvement after dimethylaminoarglabin hydrochloride treatment. Patients with lung and ovarian cancer responded particularly well to dimethylaminoarglabin hydrochloride treatment as about 64% of lung cancer patients and 66% of ovarian cancer patients had considerable improvement. Dimethylaminoarglabin hydrochloride had little toxicity and did not suppress hematopoiesis. During the trial, no negative responses of the gastrointestinal tract or hair follicles were registered.

In patients with primary liver cell carcinoma, the size of the liver was reduced over 50% in two patients and approximately 50% in another patient after treatment with lyophilized-dimethylaminoarglabin hydrochloride. Patients reported an improved state of mind and appetite. Pain in the right hypochondrium disappeared.

Immunologic status of the patients was evaluated using standard methods of rozette-formation and phagocytosis. These indices were studied prior to treatment, during treatment and after treatment. Blood samples were taken from a finger. Analysis of the average immunological values for this patient group revealed a positive response to treatment. On days 3–5 of treatment, the number of T-lymphocytes was reduced from 57% to 40.1%, the number of T-helper lymphocytes was reduced from 50% to 37.3% and the neutrophil adhesiveness decreased from 42% to 28.5%. Undifferentiated lymphocytes increased from 21.5% to 42.2%. A general change in the ratio of T-helper lymphocytes to T-suppressor lymphocytes was due to an increase of T-suppressor lymphocytes. The number of B-lymphocytes and phagocytic activity remained stable. Total number of leukocytes increased up to $9.4 \times 10^9/L$ and the total number of lymphocytes increased as well. The levels of all types of immunoglobulins increased.

By day 20 of treatment, all indices returned to normal. In some patients, indices returned to normal by day 14. In patients that were analyzed 30 days after treatment, a significant increase in the number of T-lymphocytes and adhesiveness of neutrophils was observed.

A three to six month lag in dimethylaminoarglabin hydrochloride production halted the first clinical trial. In a second clinical trial, dimethylaminoarglabin hydrochloride was given to 72 patients (61.1% male and 38.9% female) with stage IV cancer from different localizations. Among the patients, 25% had carcinoma of the stomach, 16.7% had liver cancer, 18.1% had lung cancer and the remaining 40.2% had esophageal, breast, ovarian, pancreatic, brain or lymphosarcoma. Patients with poorer states had metastases to the liver (25%), retroperitoneal lymph nodes (25), ascites (22.2%) and exudative pleuritis (11.1%). Some of these patients had been previously treated with dimethylaminoarglabin hydrochloride in the first clinical trial. Results from the second clinical trial are summarized in Table VII.

TABLE VII

| RESPONSE | % of Patients |
| --- | --- |
| Total Regression | — |
| Partial regression over or equal to 50% decrease of tumor or metastasis | 61.1 |
| Absence of dynamics or stabilization | 31.9 |
| Progression | 7.0 |

Use of dimethylaminoarglabin hydrochloride as an antitumor cytostatic in solid tumors has a number of advantages. The preparation has no side effects, it does not suppress hematopoiesis, it normalizes the functional condition of immune system, and has no allergenic effect. As a cytostatic, it is particularly efficient for primary cancer of the liver and other solid tumors complicated with polyserositis. Partial regression of tumor was observed in 61.1% cases; stabilization of process—in 31.9% cases and recurrence was observed in only 7.0%. 88.9% of patients (64 of 72) responded to therapy: no response was observed in 11.1% (8 of 72).

The following are abstracts from the case records of selected patients, who received dimethylaminoarglabin hydrochloride monochemotherapy.

Patient M, age 55, case number 305, entered the hospital with multiple nodes on the skin of thorax and abdomen, ulcer on the place of extripated breast, and induration on the right breast. In a previous hospital stay, a radical mastectomy had been performed at Sakhalinsk Oncology Center due to breast cancer. After surgery, she received 6 courses of polychemotherapy with cyclophosphamide and methotrexate.

Symptomatic therapy was recommended because of recurrence of the process. Before treatment, the abdomen and thorax skin had multiple metastatic nodes with sizes ranging from 0.5 to 1 cm. On the left side of thorax, an ulcerous surface, approximately 10×12 cm, was present. The right breast was deformed because of infiltrative metastases. Edema was present in the lower extremities.

A blood analysis before treatment revealed the following parameters: Hb-89, ESR-6 mm/hy, L-3.3, Er-3.8 ml, juv.ne-4, seg. ne-78, mon-1. The patient received 5 courses of dimethylaminoarglabin hydrochloride treatment at a total dose from 6.0 to 7.3 grams. A blood analysis, repeated after chemotherapy, revealed the following parameters: Hb-122, ESR-20 mm/h, L-10.9, Er-3.8 ml, eos-1, stab ne-3, seg, ne-64, lym-34, mon-2.

During the treatment, the ulcer was epithelized, the metastases nodes were resolved, and infiltration of the right breast decreased 50%. Edema on the lower extremities was gone.

In a 4 month old patient, case number N2225, a complete recovery from liver cancer was observed. The young patient was admitted to the surgical department of the Karaganda Cancer Treatment Center in extremely poor condition and diagnosed with embryonal carcinoma of the liver. The cutaneous integuments were of yellowish color. The patient had labored breathing. Cardiac sounds were clear, rhythmical. Ps-150 per minute. The tongue was moist, clear. The abdomen was enlarged. The liver was enlarged and indured with a smooth surface, the lower margin at the upper flaring portion of the ilium.

Ultrasonic tomography (UST) of the liver indicated that the liver was enlarged and occupied the whole abdominal cavity. The structure was dissimilar because of the foci of dissimilar structure with hydrophilic rim up to 5–6 cm, indicating a liver tumor.

Blood analysis before treatment revealed the following parameters: Hb-84, ESR-4 mm/h, L-10.9, Er-3.3 ml, eos-1, juv, ne-55, stab ne-45, seg, ne-14, lym-30, mon-5. Paracentesis of the liver was performed under the control on UST. Bare nuclei of tumor cells were observed against a background of hepatic cells with degenerative changes. The patient was diagnosed with embryonal liver cancer.

A course of dimethylaminoarglabin hydrochloride treatment, at a daily dose of 120 mg IV was started. The total dose for the course of treatment was 2040 mg. During treatment, a significant improvement was observed. The abdomen became symmetric and smaller due to the decrease in liver size.

A UST indicated that the liver projected from under the coastal arch along midclavicular line on 4 cm, the outlines are even, the structure is dissimilar because of the foci of dissimilar structure with hydrophylic rim and foci of high echogenity 2.0–2.5 cm in diameter. Conclusion: tumor with focal changes.

Blood analysis, repeated after treatment revealed the following parameters: Hb-177, ESR-4 mm/h, er.-4.0 ml, Z-9.8, eos-3, seg. ne-28, lym-53, mon-6. The child was discharged in a satisfactory condition. Two weeks later a repeated course of treatment was given, which was well tolerated by the patient.

As of early 1997, the baby's condition is satisfactory. Her mother has not reported any sign of recurrence. The palpation of the abdomen showed the liver was smooth, projects from under the margin of the coastal arch on 2 cm. The baby is believed to be cured.

Patient A, age 27, case number 543 was diagnosed with a brain tumor. The neurosurgeon excluded the possibility of operation because of the poor condition of the patient. The patient was very weak and had expressed bradykinesia of akineticorigid syndrome type. Bilateral exopthalm was reported. After the first course of dimethylaminoarglabin hydrochloride treatment, his condition was stabilized and no headaches were reported. After the second course, the condition was stable. No headaches were reported and the appetite was preserved. This case confirmed the experimental findings regarding the compound's capability to get through the blood-brain barrier.

The efficiency of dimethylaminoarglabin hydrochloride monochemotherapy was estimated according to Karnofsky scale, 1997 (Table VIII). No side effects of dimethylaminoarglabin hydrochloride therapy were reported. Mean indices of peripheral blood are shown in Table IX.

TABLE VIII

Karnofsky scale

| Estimation of the effect, in % | Description of the effect | Number of Patients abs, N | % |
|---|---|---|---|
| 90 | Ability to keep normal activities, minimum signs of the disease. | 30 | 41.7 |
| 80 | Normal activities are hardly performable, there are some signs of the disease. | 10 | 13.9 |
| 70 | Maintains himself, but is not able to work. | 24 | 33.3 |
| 60 | Needs occasional assistance, but is able to maintain himself. | 5 | 6.9 |
| 30 | Extreme invalidism | 3 | 4.2 |

TABLE IX

| Lab. indices | Before Treatment $10^{12}/l$–$10^9/l$ | During Treatment | After Treatment |
|---|---|---|---|
| Erythrocytes | 2.3–3.0 | 2.4–3.0 | 3.0 |
| Leukocytes | 4.5–5.5 | 3.5–4.0 | 4.0 |
| Lymphocytes | 8–15 | 28–35 | 15–20 |
| Thrombocytes | 2.0 (thsd) | 2.3 | 2.8 |

The indices of immune system were determined using rozette forming and phagocytosis methods. 57 patients that had received dimethylaminoarglabin hydrochloride were examined. Eleven indices of cellular and humoral immunity were measured from each patient in order to evaluate immune status. The following indices were determined on 0.05 ml of peripheral blood: absolute and relative amount of T- and B-lymphocytes, amount of non-differentiated "zero" cells, adhesion and phagocyte activity of neutrophils, hemogram, level of serum immunoglobulins. Indices were determined before treatment, on days 2, 5 and 14 of treatment, and after treatment. Table X summarizes the results before and after treatment On the 2nd–5th day of treatment, the percentage of T-lymphocytes and T-helper lymphocytes was reduced considerably. The level of non-differentiated "zero" cells increased. This population of non-differentiated cells consisted of both aged and immature B- and T-lymphocytes, and natural killer cells. No significant shifts in hemogram were noted.

Beginning with the 6th–10th day of treatment, almost all indices returned to their initial values. In two weeks, an increased ratio of T-lymphocytes and their T-helper population was registered, while the number of B-lymphocytes decreased. No changes in serum immunoglobulin levels were registered at that time.

After the treatment, a statistically insignificant elevation of T-lymphocytes percentage content was seen. Absolute numbers of T-lymphocytes increased as well as the number of T-helper lymphocytes enhancing phagocyte activity of neutrophils. There was an increased number of B-lymphocytes and also an increased amount of immunoglobulins A, M and G. The number of nondifferentiated cells was reduced.

The total number of lymphocytes in the peripheral blood was elevated. As tumors can cause both quantitative and qualitative changes in blood cells, these parameters were checked after dimethylaminoarglabin hydrochloride treatment. No shift in qualitative (morphological) composition of blood cells was identified, although some quantitative changes such as a decreased number of neutrophils and an increased number of lymphocytes was observed. This suggests a reduction lymphotoxic effects caused by the tumor. The immunologic indices correlated with the clinical findings in most cases.

TABLE X

Indices of patients' immunity before and after arglabin treatment

| Indices | Before Treatment (range) | After Treatment (range) |
|---|---|---|
| T-lymphocytes, % | 48.00 ± 1.74 (28–72) | 52.00 ± 1.42 (36–72) |
| T-lymphocytes, absolute | 0.72 ± 0.08 (0.13–1.67) | 1.14 ± 0.17 (0.18–2.99) |
| B-lymphocytes, % | 19.12 ± 1.02 (8–12) | 18.50 ± 10.0 (4–32) |
| B-lymphocytes, absolute | 0.29 ± 0.05 (0.09–0.73) | 0.45 ± 0.07 (0.05–1.16) |
| T helper cells, % | 39.12 ± 1.25 (24–52) | 45.30 ± 1.26 (28–60) |
| T suppressor, % | 10.48 ± 1.60 (00–60) | 10.50 ± 0.95 (00–24) |
| Non differentiated lymphocytes, % | 32.64 ± 1.74 (8–52) | 26.00 ± 2.21 (4–60) |

TABLE X-continued

Indices of patients' immunity before and after arglabin treatment

| Indices | Before Treatment (range) | After Treatment (range) |
|---|---|---|
| D-phag., % | 41.36 ± 0.95 (28–52) | 48.1 ± 0.93 (36–85) |
| D-phag, abs | 1.69 ± 0.26 (0.64–7.45) | 2.32 ± 0.19 (0.66–5.69) |
| Adhesion, N/ph | 39.68 ± 1.74 (24–68) | 42.40 ± 1.72 (24–66) |
| Immunoglobulins A, g/l | 1.48 ± 0.02 (1.06–2.0) | 1.97 ± 0.08 (0.90–2.84 |
| G | 14.33 ± 0.43 (11.0–22.0) | 17.91 ± 0.41 (11.6–22.0) |
| M | 1.36 ± 0.03 (1.18–1.84) | 1.53 ± 0.03 (1.20–1.84) |
| Leukocytes, $10^9$/l | 5.97 ± 0.60 (3.40–18.6) | 9.14 ± 0.61 (3.40–18.9) |
| Neutrophils, % | 4.72 ± 0.91 (0.0–23.0) | 5.45 ± 0.79 (0–20) |
| Segmentation nucleus | 61.68 ± 45.0 (23–85) | 63.05 ± 1.79 (38–88) |
| Eosinophil | 2.72 ± 0.71 (0–18) | 3.35 ± 1.30 (0–33) |
| Monocytes | 5.28 ± 2.48 (0–12) | 4.45 ± 0.44 (1–12) |
| Lymphocytes | 25.52 ± 2.02 (6–57) | 23.15 ± 1.7 (4.0–47) |

Mean values of immunological indices were evaluated with regression analysis. Functional conditions of the immune system were estimated using integral indices such as a mean intensity (correlation) expressed in relative units. That the index-intensity of the immune system increased during treatment indicates that the immune system responded to treatment.

Correlation analysis of these data indicate that during treatment, the total amount of true bound parameters increased (the number of bonds with r>0.7 increased, and the number of negative bonds was reduced).

The number of interrelations between the elements of immunity increased, namely between the lymphocyte and neutrophil elements.

Thus, the statistical data analyzed with different methods of statistical assay, indicate that dimethylaminoarglabin hydrochloride is active as an agent stimulating some immunity factors and improving the functional condition of the immune system. This indicates the immunostimulative effect of the preparation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of suppressing tumor growth in a human comprising administering to said human an amount of a first chemotherapeutic agent comprising dimethylaminoarglabin or a pharmaceutically acceptable salt thereof and a second chemotherapeutic agent effective to suppress said tumor growth in said human.

2. The method of claim 1, wherein said second chemotherapeutic agent is selected from the group consisting of alkylating agents, antimetabolites, vinca alkaloids, antibiotics and platinum coordination complexes.

3. The method of claim 2, wherein said alkylating agent is cyclophosphamide, sarcolysin, or methylnitrosourea.

4. The method of claim 2, wherein said antimetabolite is methotrexate or fluorouracil.

5. The method of claim 2, wherein said vinca alkaloid is vinblastine or vincristine.

6. The method of claim 5, wherein said chemotherapeutic agent further comprises cyclophosphamide.

7. The method of claim 2, wherein said antibiotic is rubidomycin.

8. The method of claim 2, wherein said platinum coordination complex is cisplatin.

9. The method of claim 1, wherein said first chemotherapeutic agent is administered prior to said second chemotherapeutic agent.

10. The method of claim 9, wherein said first chemotherapeutic agent is administered two hours prior to said second chemotherapeutic agent.

* * * * *